US006717029B2

(12) United States Patent
Baker

(10) Patent No.: US 6,717,029 B2
(45) Date of Patent: Apr. 6, 2004

(54) ABSORBENT ARTICLE HAVING AN IDEAL CORE DISTRIBUTION AND METHOD OF PREPARING SAME

(75) Inventor: Andrew Baker, Lawrenceville, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 123 days.

(21) Appl. No.: 09/799,071

(22) Filed: Mar. 6, 2001

(65) Prior Publication Data

US 2003/0023215 A1 Jan. 30, 2003

(51) Int. Cl.[7] ................................................ A61F 13/15
(52) U.S. Cl. .................................................... 604/378
(58) Field of Search ............................... 604/358, 367, 604/374, 375, 378, 380, 385.01

(56) References Cited

U.S. PATENT DOCUMENTS

| 3,501,813 | A | 3/1970 | Lee et al. |
| 3,518,726 | A | 7/1970 | Banks |
| 3,598,680 | A | 8/1971 | Lee |
| 3,939,240 | A | 2/1976 | Savich |
| 3,973,291 | A | 8/1976 | Kolbach |
| 3,975,222 | A | 8/1976 | Mesek |
| 3,994,047 | A | 11/1976 | Lee et al. |
| 4,016,628 | A | 4/1977 | Kolbach |
| 4,223,677 | A | 9/1980 | Anderson |
| 4,388,056 | A | 6/1983 | Lee et al. |
| 4,685,915 | A | 8/1987 | Hasse et al. |
| 4,997,428 | A | 3/1991 | Linnebur et al. |
| 5,098,423 | A | 3/1992 | Pieniak et al. |
| 5,643,238 | A | * 7/1997 | Baker .......................... 604/368 |
| 5,817,079 | A | 10/1998 | Bergquist et al. |
| 5,849,002 | A | 12/1998 | Carlos et al. |
| 5,983,457 | A | 11/1999 | Toney et al. |
| 6,068,620 | A | 5/2000 | Chmielewski |

OTHER PUBLICATIONS

International Search Report Dated Mar. 31, 2003, for application No, PCT/US02/06560, filed Mar. 6, 2002.

* cited by examiner

*Primary Examiner*—Weilun Lo
*Assistant Examiner*—Michele Kidwell
(74) *Attorney, Agent, or Firm*—Hunton & Williams LLP

(57) ABSTRACT

An absorbent article and a method for preparing an absorbent article is disclosed. The absorbent article has a core comprised of pulp, a polymer or a combination thereof. The absorbent article conforms to a certain Distribution Index (DI) or a certain Distribution Index (DI) profile that confers one or more superior properties to the core and in turn to the absorbent article, such as superior absorbency efficiency and superior cost efficiency. The method for preparing the absorbent article uses DI values (e.g., $DI_{max}$, $DI_{min}$, $DI_{male}$ and $DI_{female}$) or a DI profile as design parameters for providing absorbent articles having one or more superior characteristics.

76 Claims, 8 Drawing Sheets

ABSORBENT ARTICLE HAVING AN IDEAL CORE DISTRIBUTION AND METHOD OF PREPARING SAME

FIELD OF THE INVENTION

The present invention relates to absorbent articles, and to methods for preparing the same. In particular, the absorbent articles include cores characterized by a Distribution Index or Distribution Index profile to provide improved absorbency, improved cost efficiency and/or other superior characteristics.

BACKGROUND OF THE INVENTION

Traditionally, disposable absorbent garments such as infant diapers and training pants, adult incontinence products, and other such products are constructed with a moisture-impervious outer backing sheet, a moisture-pervious body contacting inner lining sheet, and a moisture-absorbent core sandwiched between the liner and backing sheets.

Much effort has been expended to develop cost-effective absorbent cores that display optimal liquid absorbency and retention. In many applications, it is desirable to form an absorbent article having a zoned absorbency profile where different predetermined regions have different basis weights of fibers per unit area, and, therefore, different absorbencies. Such variation in basis weight across a fibrous article can, for example, enhance the efficiency of the fibrous article in end usage as disposable diapers and sanitary napkins.

For example, U.S. Pat. No. 4,685,915 to Hasse et al. discloses a disposable diaper wherein a central portion of its absorbent core has a higher density and higher basis weight per unit area than longitudinally placed end portions of the absorbent core. The disclosed absorbent cores may comprise a mixture of hydrophilic fibers and discrete particles of a highly absorbent material such as, for example, hydrogel material. The absorbent cores are described as having a central portion that is preferably substantially uniformly dense and of uniform basis weight throughout its extent, and where the ratio of the average density of the central portion to the average density of each of the end portions is about 2 to 1 or greater, and more preferably, 2.5 to 1 or greater.

U.S. Pat. No. 5,849,002 to Carlos et al. discloses a disposable diaper in which the absorbent core material is distributed in such a way that three zones are made inside of it, one of liquid reception, a zone of distribution-storage, and finally an anti-leakage zone. The reception zone is described as being placed where generally the user discharges urine while using the diaper. This zone is described as being less dense and has a lower specific gravity than the distribution-storage zone that fully surrounds it, in such a way that when liquid flows into the reception zone it is immediately absorbed and flows towards the distribution-storage zone, which will distribute the liquid to every zone of the diaper and where it will then remain until the diaper is disposed.

U.S. Pat. No. 5,817,079 to Bergquist et al. discloses absorbent products having discrete areas of dry fibrous materials such as fluid-repellent materials that are precisely placed in various plains within the product so as to provide barriers to bodily fluid leakage from the product. A preferred embodiment is described as having hydrophilic fibers placed around the parameter of a central absorbent area of an absorbent product to discourage and/or prevent side or end leakage from the product.

U.S. Pat. No. 5,098,423 to Pieniak et al. discloses a disposable diaper that is particularly configured for improved fit and comfort, as well as to provide enhanced absorptive capacity and leakage-resistant characteristics. The disposable diaper is described as having improved fit and comfort that is achieved by providing the diaper with a relatively thin, narrow absorbent panel, with the panel configured to provide desirably high absorbency efficiency for enhanced performance characteristics. The diaper is described as having an absorbent panel that is configured to exhibit sufficient and inherent absorbency to provide an impact zone with an absorbent efficiency index of at least 1.5. This absorbency efficiency index is determined by ascertaining the absorptive characteristics of a diaper's absorbent panel as it relates to the bulk of the panel. The absorbency efficiency index relates to the relationship between the diaper bulk and absorptive capacity. This index is described as being determined by dividing the urine volume at the $90^{th}$ percentile level in the impact zone (of a mid-size diaper) by the volume of the impact zone absorptive medium. The impact zone is defined as the 6 inches of panel located at the second and third fifths of the panel length, as measured from the front of the diaper.

U.S. Pat. No. 4,997,428 to Linnebur et al. discloses a hygienic disposable article used as diaper, which possesses an absorbent body enhanced with expandable material. The article is described as having expandable material that is to be applied along the direction of the longitudinal access of the diaper, in decreasing quantity outward from the crotch area in such a way that the concentration of the expandable material in the crotch area is 8% to 40% of the weight of the absorbent body, while in the area of the waist it is 1% to 7% thereof. The disposable article is described as achieving an optimal distribution of the absorbent components of the diaper in accordance with the distribution pattern of the fluid excreted from the wearer.

In the general practice of forming fibrous materials as absorbent articles, including absorbent cores, it has become a practice to utilize a fibrous sheet of cellulosic fiber's, or other suitable fibers, which is fiberized in a conventional fiberizer or other device to form discrete fibers. The discrete fibers which then are entrained in an air stream or airflow and directed to a forming surface whereon the fibers are deposited to form a pad of fluff, i.e. a non-woven mat of randomly arrayed fibers containing substantial interstitial void space and being highly compressible in character.

The forming surface utilized in such system typically is constructed as a wire or screen grid and typically employs pneumatic flow means such as a vacuum suction apparatus to define a differential pressure zone on the forming surface and impose a pressure differential thereon. The air in the air entrained fiber stream is passed through the openings or perforations in the screened grid of the forming surface. The use of vacuum suction to draw the air entrained fiber stream to the forming surface, with the passage of the air component through the forming surface, is highly efficient and lends itself to high speed commercial operations.

In the prior practice of forming laid fibrous articles, various means have been provided in the art for providing the fibrous article with gradiations or variations in basis weight across the surface thereof. Various means, have been proposed for producing gradiations of basis weight.

For example, U.S. Pat. No. 4,388,056 to Lee et al. ("the '056 patent") discloses an apparatus for continuously forming an air-laid fibrous web, comprising a laydown drum having a circumferentially segmented annular-shaped plenum comprising a multiplicity of circumferentially placed transverse plenum segments, and a partially masked foraminous laydown surface having oppositely contoured, cyclically undulating side edges defining cyclically circumferentially placed relatively wide masked and relatively narrow masked transverse areas of the surface, which together define the radially outward facing boundary of the plenum. Constant differential pressure means are employed for drawing air through the foraminous laydown surface and the plenum from an air-entrained-fiber deposition chute as the drum is rotated. The specific improvement described in the '056 patent comprises stationary adjustable air flow modulating means (shutter plates) disposed adjacent the radially inwardly disposed boundary of an arcuate portion of the plenum circumferentially spanning a plurality of the transverse plenum segments. In such manner, the pressure across the relatively widely masked transverse sections of the laydown surface can be adjusted without substantially affecting the pressure across the relatively narrow masked transverse sections of the laydown surface.

This apparatus purportedly permits the formation of a fibrous web severable into uniform, contoured articles, such as fibrous absorbent cores for disposable diapers, having relatively thick narrow and absorbent crotch areas, and relatively thin waistband regions, without stepwise basis weight gradients. Thus, the areas of the foraminous laydown surface (screen) having the largest pressure differential across them (i.e., the narrow areas) experience greater fiber buildups or accumulations than the areas of the screen having lower pressure differentials across them (i.e., the wide areas). The narrow areas correspond to the crotch regions of the web articles and the wide areas correspond to the waistband regions thereof.

Although the apparatus disclosed in the '056 patent is alleged to provide a smooth basis weight gradiation in the machine direction (i.e., longitudinally) in the fibrous articles formed thereon, as noted particularly with reference to FIGS. 7 and 8 of this patent, the basis weight gradiation of the fibrous article is both longitudinally and laterally symmetrical in distribution. Accordingly, the greatest basis weight occurs in a circular shaped region centered at the crotch with the basis weight uniformly radially decreasing therefrom, such that lines of nominally equal basis weights describe concentric circles radiating outwardly from such central region of highest basis weight. This design provides a high basis weight in the frontal crotch region where same is usefully employed. For reasons of liquid retention, however, it is more advantageous to provide a longitudinally extending central region of high basis weight relative to the longitudinal peripheral margins, and further to provide a higher basis weight in the front panel of the fibrous article relative to its rear panel (the front and rear panels being considered here as the demarcated opposed symmetrical portions produced when the fibrous article is folded along a lateral fold line midway along its longitudinal extent). In comparison to these optimal basis weight characteristics of the fibrous web article, the fibrous articles produced by the apparatus of the '056 patent are seen to be deficient, particularly in the steady decline of such articles basis weight along the full longitudinal dimension of the front and rear panels, from a point centered at the crotch region of the article.

U.S. Pat. No. 3,939,240 to P. P. Savich discloses a method of dry forming fibrous pads by means of a condenser roll having three-dimensional cavities circumferentially disposed about the periphery thereof. The cavities each have foraminous bottom and side surfaces, with the surface area of the cavity being greater than the surface area of the opening into the cavity. Vacuum is applied through the foraminous surfaces of each cavity to pull the air component of a fibers/air suspension through the foraminous surfaces, thereby depositing the fibers carried in the air suspension onto the cavity surfaces. A transfer conveyor is proximately disposed to the cavity opening at its discharge position and vacuum also is supplied through the transfer conveyor, to transfer the fibrous layer from the cavity onto the conveyor. The fibers deposited on the transfer conveyor are confined to an area substantially equal to the surface area of the cavity opening, so that the fibers are consolidated as they are transferred from the cavity onto the conveyor, forming fibrous pads having a greater basis weight than the basis weight of the fibrous layers formed in the cavities. This patent, in addition to embodiments disclosing the formation of discrete fibrous pads unassociated with any fibrous web, discloses an embodiment in which the outer periphery of the forming roll surrounding each cavity is also foraminous. In such manner, the fibrous pads formed from the fibrous layers within each cavity will be integrally joined with fibrous web sections of a lower basis weight.

U.S. Pat. No. 4,223,677 to J. E. Anderson discloses an absorbent fibrous structure that includes intermingled absorbent fibers of a varying length up to about 6.35 millimeters. The fibers are disposed in different classified layers having differing weighted average fiber length in each of the layers, with the weighted average fiber length decreasing from layer to layer in a direction from one outer surface to the opposite outer surface. The separate layers of the absorbent pad are not disclosed as having any varying weight within the respective layers, so that the basis weight is constant along the longitudinal and transverse dimensions of the pad.

U.S. Pat. No. 3,973,291, to C. G. Kolbach discloses an apparatus for forming fibrous pads comprising a pad assembly having spaced three-dimensional pad-receiving compartments, each separated by air-impermeable regions. The pad-receiving compartments are defined by lower air-permeable surfaces and air-impermeable side walls extending outwardly therefrom. The side wall sections of each compartment are movable relative to the lower air-permeable surface to assist in releasing formed pads from the compartments.

In column 8, lines 41 et seq. it is alleged that the patentee has discovered that formation of a profiled fibrous pad, i.e., one with a varying basis weight, "cannot be controlled within close tolerances by establishing a different amount of open area through which air can be drawn by a vacuum box through different predetermined regions underlying the different predetermined sections of the pad-receiving compartment in which different weights of fibers per unit area are to be deposited". Based on this discovery, it is contended that "the only effective means for establishing different weights of fiber per unit area in different predetermined regions of a fibrous pad, while maintaining close tolerances, is to completely form each predetermined region with a specific weight of fibers per unit area therein substantially independently of the formation of every other predetermined region having a different weight of fibers per unit area therein". The disclosed method thus involves completely masking off a source of vacuum to all sections of each pad-receiving compartment except the section in which region a fibrous pad having a particular weight of fibers per unit area is to be formed. After this region has been completely formed, the vacuum source underlying the formed region is completely masked to the passage of air, and a second section of each pad-receiving compartment is exposed to vacuum to form a predetermined region on the pad having a different weight of fibers per unit area therein. Thus, the patentee discloses a serial masking-unmasking sequence to provide the finished article.

U.S. Pat. No. 3,501,813 to C. A. Lee et al. discloses a method and apparatus for forming a single integral web of air-laid fibrous material with non-uniform cross-sectional thickness. The disclosed apparatus employs a carrier moving at uniform rate whereon first and second quantities per unit time of loose fibrous material are conveyed by air and deposited on first and second different portions of the carrier. The uneven distribution of material on the foraminous carrier is achieved by providing the air stream with a velocity profile in which certain portions have a higher velocity than the adjoining portions and convey a greater amount of material to associated portions of the carrier, the varying velocities are achieved by creating a greater vacuum or suction behind the associated portions of the foraminous carrier than behind adjacent portions so as to draw the air through the screen at the same rate as it arrives at the screen. This in turn is achieved by shielding a portion of the carrier from the air stream while deflecting the air stream toward the unshielded portion.

As shown in FIG. 5 of the '813 Lee et al. patent, baffles are provided to constrict the conduit through which air is delivered to the carrier, with valves being provided to permit the establishment of a lower pressure behind certain portions of the carrier than behind adjacent portions. The baffles and valves are both selectively operable to provide the web with a predetermined profile or cross-sectional configuration. The web produced by such apparatus, as disclosed in column 4, lines 1–3, has a raised or thick center portion flanked by substantially thinner edge portions. Thus, baffles are provided upstream of the forming surface and valves downstream from the forming surface, with respect to the path of the air flow therethrough. Each of the baffles is in the form of a flat plate beveled at its innermost end and positioned in a slot defined by flanges, which by virtue of the inclination of the flanges, cause the baffles to extend inwardly from opposite sides of the central conduit and be inclined in the direction of flow of the air stream. Accordingly, the baffles constrict the conduit within the delivery duct to narrow the air stream to a centrally disposed vertically oriented flow and thereby increase velocity of the air stream in the central area of the conduit.

The foraminous carrier is supported by a vacuum box that also serves to control the passage of air through the carrier. The vacuum box includes a grid plate provided with a plurality of openings that affords communication between the vacuum chamber and the surface of the grid plate, thereby creating a section that removes air arriving at the surface of the plate. Each opening in the grid plate has associated therewith a valve that permits selective control of air pressure at each opening and consequently, permits variations in the degree of suction across the grid. The web formed on the carrier screen is removed therefrom by a take-off roll associated with nozzles proximate thereto that direct jets of air outwardly through the carrier screen thereby assisting in the separation of the web from the screen, and cleaning the screen of adhering fibrous particles.

U.S. Pat. No. 3,598,680 to C. A. Lee discloses a tandem air former for forming a fibrous web of non-uniform cross-sectional thickness, by air-laying fibrous material at a first station and then air-laying additional fibrous material at a second station downstream from the first to overlap at least partially the fibrous material deposited at the first station. A pressure differential is maintained across the web during formation, to cause air to flow through the thicker portion of the web as well as the thinner portions at substantially the same rate as it approaches the web. The air flow passageway to the foraminous carrier is defined in part by plates that are adjustable transversely of the web being formed, i.e., the respective opposed plates may be shifted toward or away from one another to vary the width of the air stream passing between them and, in consequence, the width of the pad being deposited on the web.

U.S. Pat. No. 3,975,222 to F. K. Mesek discloses a disposable diaper assembly comprising an absorbent fibrous panel that is double contoured, whereby the diaper is centrally contoured in the transverse and longitudinal directions to produce a smooth peak on one major surface. Two rolls of compacted wood are provided to feed a source of short cellulosic fibers to a grinding mill from which a stream of fibers is blown downwardly through a duct onto a belt as a layer. The patent discloses that the duct may be baffled to allow more fibers to be concentrated at the central portion of the web. Another method comprises grinding fibers at one station and depositing them to produce a continuous web at the maximum width desired and grinding fibers at another station and depositing them downstream along a band of lesser width on top of and along the median of the first continuous web. A longitudinal contour of the fibrous web is achieved by varying the speed at which fibers are deposited on the belt, so that by decreasing the deposition rate the marginal areas of reduced thickness are produced and correspondingly, by increasing the deposition rate, the thickened central contour portion is produced. The contour thickness is preferably formed to provide a ratio of apex thickness to corner thickness in the range of 1.5:4.

U.S. Pat. No. 3,994,047 to C. A. Lee et al. discloses apparatus for making two-layer composite pads formed simultaneously on a twin wire arrangement, with the units of one layer being of hourglass and the other, ovate in shape. The layers are formed on respective foraminous carriers in a forming chamber. In the disclosed system, it is necessary to keep the respective forming screens in register with one another inasmuch as the webs formed thereon are subsequently joined to form the aforementioned composite. For such purpose, the respective forming screens have registration indicia that may be sensed as, for example, by an electric eye, to indicate any misregistration whereby the appropriate tension roll for the respective forming screen is adjusted to maintain registration. In order to drive air through the laydown fibrous web layers at the same rate at different portions of the forming path, the pressure differential and the respective forming layers increase in the direction of travel of the carrier screens by separately controlled air flow through suction boxes associated therewith. Each of the suction boxes includes a damper for controlling the rate of flow of air through each of the boxes. The forming chamber also has a perforated wall opening through which additional air may be admitted to the forming chamber.

A removal means is provided at the exit end of the forming chamber to remove any excess fibers deposited on the respective carriers. This removal means includes a snout, which in turn includes a septum and walls defining openings through which air is sucked by a blower at relatively high velocity. The walls of the snout are disposed relatively close to the tops of formed layers of fibers to provide a rush of air over the exposed surfaces thereof. This shears fibers from the surfaces of the layers and entrains the fibers in the air stream removed therefrom. The foraminous carrier screens in this system include open areas on which the respective fibrous web components are formed, the areas outside of such patterned open areas being impervious (impermeable) to air flow.

U.S. Pat. No. 4,016,628 to C. G. Kolbach ("the '628 patent) discloses an apparatus for forming a fibrous web that includes a medial portion integrally joined through the randomly arranged fibers thereof to flanking side portions and flanking end portions, the medial portion having a greater basis weight and thickness than the respective flanking side and end portions. The patent discloses at column 3, lines 29–40 that the higher basis weight medial portion of the fibrous web can be substantially uniform in basis weight or can be profiled, e.g., with the center section of the medial portion being provided with a greater basis weight of fibers than the flanking end sections (for use as disposable diapers for girls and, alternatively, a forward section of the medial portion being provided with a greater basis weight of fibers therein than a rearward section thereof, as when the fibrous web is used as a disposable diaper for boys). In addition, it is disclosed at column 3, lines 41–47 that the specific shape of the medial portion can be varied within wide limits, such as being substantially rectangular or contoured to include a reduced width crotch region that provides a more conformable structure in the perineal region of a wearer.

Embodiments of the product fiber web are shown in FIGS. 11, 13 and 15 of the '628 patent, wherein the medial portion of the web is profiled to itself to have different basis weights in different predetermined sections thereof, such as the medial portion having a center section of greater basis weight than the adjoining end sections of the medial portion. FIGS. 12 and 16 illustrate a configuration wherein a greater basis weight section of the medial portion is provided on the forward half thereof.

The disclosed apparatus employs a foraminous forming surface and at least one vacuum box under a discrete section of the forming surface. The foraminous forming surface and the vacuum box are moved in registration with each other through a web forming area so that the same region of the foraminous forming surface is always in overlying relationship to the vacuum box. In operation, an air suspension of fibers is directed onto the surface of a condenser roll assembly, having a foraminous forming surface disposed thereon with circumferentially spaced, three-dimensional compartments therein. Downstream therefrom may be disposed embossing rolls having corresponding surface recesses therein for embossing the fibrous web, to provide surface contours thereon that channel liquids so that the full absorbent capability of the fibrous web is utilized.

The condenser roll assembly includes an air-pervious condenser roll including a perforated cylindrical metal shell and a porous screen secured about the periphery of the shell. The three-dimensional compartments are established by providing discrete cutout regions in the porous screen and cylindrical metal shell and securing a foraminous member to the lower surface of the shell to bridge each cutout region and thereby form the bottom wall of the three-dimensional compartment. In this manner, the porous screen outside the three-dimensional compartments and the foraminous member constituting the lower surface thereof together provide a forming surface for the condenser roll. A vacuum box assembly is mounted within the condenser roll secured to a driving axle so as to be concurrently rotated with the cylindrical shell. The vacuum box assembly includes a plurality of circumferentially spaced vacuum boxes attached to a cylindrical hub, with the outer edges of the sidewalls of the vacuum boxes defining an opening into the vacuum box of the same shape as the three-dimensional compartments, when aligned therewith. Since the cylindrical shell and the vacuum box assembly are concurrently rotated at the same angular velocity, each vacuum box will underlie its respective compartment throughout the entire path of rotation. Removal of the formed web from the condenser roll is effected by terminating the partial vacuum through the forming surface. This is achieved by a masking member circumferentially extending in coaxial manner with the condensing roll and the vacuum box assembly, and interposed therebetween. The masking member is perforated over a portion of its length and is imperforate on the lower section.

Accordingly, the condenser roll and vacuum box assembly during its travel will encounter the imperforate portion of the masking member, thereby blocking the vacuum imparted to the formed web, so that the web may be removed by a take-off conveyor to which vacuum is applied. The masking member is not rotated, so that the condenser roll and vacuum box assembly pass circumferentially adjacent to the masking member over its full circumferential extent. Vacuum is provided to the forming surface by suction through an annular passage in flow communication with the vacuum boxes. The portions of the interior of the condenser roll are in flow communication with a second annular passage with a reduced vacuum level being imposed thereon. The patent states at column 12, lines 56–62 that since the entire forming surface of the condenser roll is exposed to vacuum for the same period of time, a greater effective or total volumetric air flow will be established through the bottom walls of the three-dimensional compartments, which are subject to a greater partial vacuum than the surfaces flanking the three-dimensional compartments. This greater effective volumetric air flow results in the deposition of a greater weight of fibers in each of the three-dimensional compartments than on the foraminous surface regions surrounding the three-dimensional compartments. The drawings of this apparatus, such as FIG. 3, indicate that the three-dimensional compartment is relatively shallow and is bounded by radially extending wall surfaces that appear to be perpendicular to the forming surface.

In a modified embodiment of the invention, as shown in FIGS. 17–19 of the '628 patent, a masking member is employed in which the imperforate circumferential portion has at one end thereof "finger portions" that underlie the three-dimensional compartments at their extremities. These finger portions are followed circumferentially by a central blocking portion of the mask member which in turn underlies the central portion of the three-dimensional compartment when same is passed over the masking member. The circumferential extent of the finger portions is greater than the circumferential extent of the central blocking portion of the masking member, whereby the central region of the three-dimensional compartment will be exposed for a greater period of time to the vacuum, to achieve formation of thickened central portions of the three-dimensional compartments.

Finally, the '628 patent states at column 15, lines 2–7 that "it is within the scope of this invention to provide a fluid impervious coating directly on the forming surface of the condenser roll in the form of a transverse stripe disposed intermediate adjacent three-dimensional compartments to achieve direct formation of discrete fibrous webs on the forming surface." It is apparent that this coating serves as a fiber deposition blocking means to segment the web during laydown, in discrete segments.

U.S. Pat. No. 3,518,726 to C. T. Banks ("the '726 patent") discloses an apparatus for making sanitary napkins from fluff derived from wood pulp that has been disintegrated. A forming drum is employed that has on its cylindrical surface a series of planar chord-like plate members that are perforated. Each plate has perforations more closely spaced relative to one another in the central portion of the plate as compared to the end segments of the chord-like plates, wherein the perforations are more distantly spaced relative to one another. The forming drum is in gas flow communication with vacuum suction means, whereby areas of fluff deposited on the drum compartment are of greater thickness at their centers relative to their ends, due to the arcuate shape of the side plates defining each compartments on the drum periphery. In addition, more fluff collects in the central regions of the cavities than in the end regions due to the fact that the spacing between holes is less in the central regions than in the end regions. The resulting pad therefore is thicker in its central region.

The '726 patent also discloses an embodiment wherein a compressed, high-density segment is provided for embedment in one of the flat faces of the pad. In this embodiment, a second assembly takes disintegrated pulp fibers and collects some on a forming drum that is composed of a cylinder of perforated sheet material, with a vacuum box in communication with a central opening through the rotatable drum for maintaining vacuum therein. An end closure plate portion extends across and within the forming drum, being sealed with respect to the inner surface thereof. In this fashion, only about one-half of the forming drum has suction applied to it. This forming drum is in close-spaced relationship to a similar forming drum, whereby each collects fluff on its exterior surfaces for discharge therefrom between the drums in the form of a continuous batt. The batt then is debulked between compression rolls and indented at spaced intervals, following which the batt passes through an embossing assembly that provides a pattern of pyramidal-shaped depressions therein. The batt then is cut into segments and transmitted by conveyor means to the first-mentioned forming drum, on which the high-density segment is centrally disposed on the forming cavity and overlaid with fluff. The resulting pads, containing the high-density segments on their lower faces, are cut in a cutter assembly and passed to a wrapping means whereon a gauze web is folded around the individual pads, pleated and severed to form the individual sanitary napkin.

U.S. Pat. No. 5,983,457, to Toney et al., discloses an inlet plenum apparatus for delivering a uniform mass of airborne cellulose for other natural and synthetic fibers—including all forms of superabsorbent, fibers used for absorbent applications such as disposable diapers—to an apparatus employing a rotating drum containing a foraminous pad forming system and depositing it on the pad forming system in a uniform layer. The apparatus employs an inlet plenum having a specific shape to slow the air flow from the conveying line into the forming area by specified amounts to result in improved uniformity of the pad.

As is apparent from the foregoing, prior documents have presented a variety of systems for producing variant basis weight articles by air-laying of fibers, as well as numerous means of removing the laid fibrous article from the forming surface. Yet, none of these proposed techniques provides cores having an optimal core geometry, or any means for attaining an optimal core geometry in a core.

It is highly desirable to attain cores having a core geometry, or in particular a basis weight distribution, which results in an improved or superior characteristic, such as improved absorbency, cost-efficiency, fit, comfort, appearance, compatibility for males and females (e.g., for unisex use), longevity or a combination thereof, for example, without limitation. It also is highly desirable to have a method for characterizing and comparing the core geometry of various cores in a way that is simple and accurate, and that provides consistent results when performed by various testers.

SUMMARY OF THE INVENTION

It is a feature of the invention to provide a core, for use in absorbent articles, having a superior characteristic, such as improved absorbency, cost-efficiency, fit, comfort, appearance, compatibility for males and females (e.g., for unisex use), longevity, or a combination thereof. It is a further feature of the invention to provide a method for preparing a core having a superior characteristic, such as improved absorbency, cost-efficiency, fit, comfort, appearance, compatibility for males and females (e.g., for unisex use), longevity or a combination thereof. It is a further feature of the invention to provide a means or method for determining a Distribution Index for a core of an absorbent article.

One embodiment of the invention is an absorbent article, that includes a core comprised of pulp, a polymer or a combination thereof, wherein the core has a maximum Distribution Index ($DI_{max}$) of at least about 6,000 g/m$^3$. A further embodiment of the invention is an absorbent article that includes a core comprised of pulp, a polymer or a combination thereof, wherein the core has a Distribution Index$_{i,j}$ ($DI_{i,j}$) at −5,0 of at least about 5,750 g/m$^3$ or a Distribution Index (DI) at 10,0 of at least about 4,250 g/m$^3$.

An even further embodiment of the invention is an absorbent article that includes a core comprised of pulp, a polymer or a combination thereof. The core has a Distribution Index $_{i,j}$ ($DI_{i,j}$) at −5,0 of at least about 5,750 g/m$^3$, a Distribution Index $_{i,j}$ ($DI_{i,j}$) at 0,0 of at least about 6,000 g/m$^3$, a Distribution Index $_{i,j}$ ($DI_{i,j}$) at 5,0 of at least about 5,750 g/m$^3$, a Distribution Index $_{i,j}$ ($DI_{i,j}$) at 10,0 of at least about 4,250 g/m$^3$, and a Distribution Index $_{i,j}$ ($DI_{i,j}$) at 15,0 of at least about 3,250 g/m$^3$.

A still further embodiment of the invention is an absorbent article that includes a core comprised of pulp, a polymer or a combination thereof. The core has a first Distribution Index ($DI_{max}$) measured at a male insult point, and a second Distribution Index ($DI_{female}$) measured at a female insult point, wherein the difference between the $DI_{male}$ and the $DI_{female}$ is at most about 1,000 g/m$^3$.

Another embodiment of the invention is an absorbent article that includes a core comprised of pulp, a polymer or a combination thereof. The core is characterized according to general formula I:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

wherein N is the total number of core cells of the core, each core cell of the core corresponding to each of a plurality of 0.75 inch squares on a predetermined grid;

wherein T is each positive integer from 1 to N, each positive integer corresponding to each core cell of the core in numerical order;

wherein $DIST_T$ is a distance in centimeters (cm) between the center of the core cell corresponding to T and point i,j;

wherein $BW_T$ is the basis weight of each core cell, each core cell corresponding to each value for T; and wherein i,j is a coordinate representing a point on the core.

Yet another embodiment of the invention is an absorbent article prepared by a process comprising forming a core according to a predetermined maximum Distribution Index ($DI_{max}$), and placing or forming the core into an absorbent article. The core is comprised of pulp, a polymer or a combination thereof. A further embodiment of the invention is an absorbent article prepared by a process comprising forming a core having a Distribution Index$_{i,j}$ ($DI_{i,j}$) at −5,0 of at least about 5,750 g/m³ or a Distribution Index$_{i,j}$ $DI_{i,j}$) at 10,0 of at least about 4,250 g/m³, and placing or forming the core into an absorbent article. The core is comprised of pulp, a polymer or a combination thereof.

A still further embodiment of the present invention is an absorbent article prepared by a process comprising forming a core having a Distribution Index$_{i,j}$ ($DI_{i,j}$) at −5,0 of at least about 5,750 g/m³, a Distribution Index$_{i,j}$ ($DI_{i,j}$) at 0,0 of at least about 6,000 g/m³, a Distribution Index$_{i,j}$ $DI_{i,j}$) at 5,0 of at least about 5,750 g/m³, a Distribution Index$_{i,j}$ ($DI_{i,j}$) at 10,0 of at least about 4,250 g/m³; and a Distribution Index$_{i,j}$ ($DI_{i,j}$) at 15,0 of at least about 3,250 g/m³. The core is comprised of pulp, a polymer or a combination thereof. An even further embodiment of the invention is an absorbent article prepared by a process comprising forming a core having a first Distribution Index ($DI_{male}$) measured at a male insult point, and a second Distribution Index ($DI_{female}$) measured at a female insult point. The difference between $DI_{male}$ and $DI_{female}$ is at most about 1,000 g/m³.

Another embodiment of the invention is an absorbent article prepared by a process comprising selecting a Distribution Index $_{i,j}$ ($DI_{i,j}$) [or Distribution Index $_{i,j}$ ($DI_{i,j}$) profile] and forming a core wherein the DI [or DI profile] is characterized by the general formula (I):

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

wherein N is the total number of core cells of the core, each core cell of the core corresponding to each of a plurality of 0.75 inch squares on a predetermined grid;

wherein T is each positive integer from 1 to N, each positive integer corresponding to each core cell of the core in numerical order;

wherein $DIST_T$ is a distance in centimeters (cm) between the center of the core cell corresponding to T and point i,j;

wherein $BW_T$ is the basis weight of each core cell, each core cell corresponding to each value for T; and wherein i,j is a coordinate representing a point on the core.

Yet another embodiment of the invention is an absorbent article that includes a core comprised of pulp, a polymer or a combination thereof. The core has a Distribution Index$_{i,j}$ ($DI_{i,j}$) that is substantially the same at a first insult point and a second insult point, where the first insult point is the insult point at commencement of use of the absorbent article, and the second insult point is the insult point after use of the absorbent article. Still another embodiment of the invention is a method for preparing an absorbent article, which comprises: selecting a Distribution Index at a point on a core, or selecting a Distribution Index profile for a core; forming the core according to the selected Distribution Index or Distribution Index profile; and placing or forming the core into the absorbent article. The core is comprised of pulp, a polymer or a combination thereof.

A further embodiment of the invention is a method for determining the Distribution Index (DI) of an absorbent article, which comprises: obtaining a core; removing samples from the core; determining the basis weight at a point or plurality of points on the core; determining the distance of each point from a predetermined point; and calculating the DI Index for the insult point according to general formula (I):

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

wherein N is the total number of core cells of the core, each core cell of the core corresponding to each of a plurality of 0.75 inch squares on a predetermined grid;

wherein T is each positive integer from 1 to N, each positive integer corresponding to each core cell of the core in numerical order;

wherein $DIST_T$ is a distance in centimeters (cm) between the center of the core cell corresponding to T and point i,j;

wherein $BW_T$ is the basis weight of each core cell, each core cell corresponding to each value for T; and wherein i,j is a coordinate representing a point on the core.

DETAILED DESCRIPTION OF THE PREFERRED EMBODIMENTS

Figure 1:
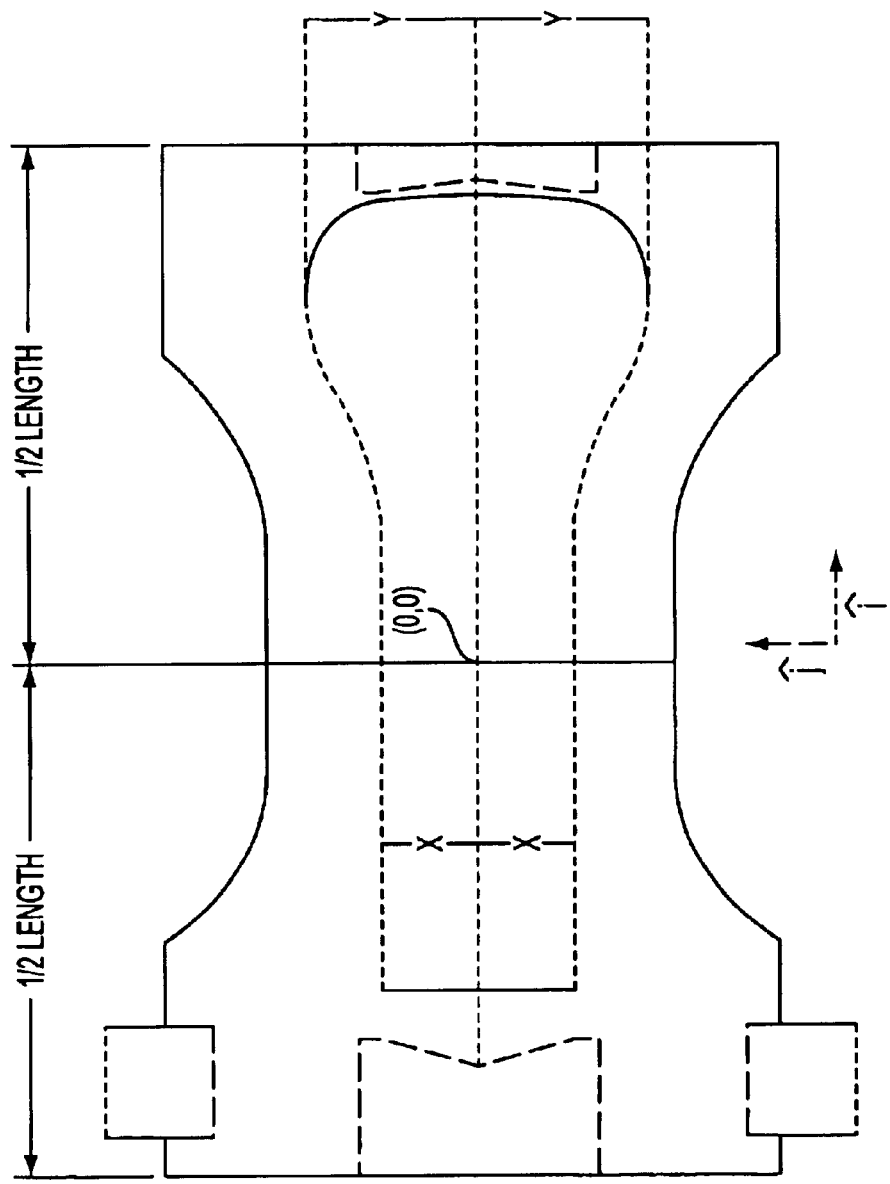
FIG. 1 is a pictorial representation of the position of points i,j on a core in an absorbent article in accordance with an embodiment of the invention.

As used herein, "absorbency" refers to the functional capacity and the rate at which absorption occurs, as measured by absorption under load (AUL). "Air permeability," as used herein, refers to the amount of air that the surface permits to pass through during a specified amount of time relative to another surface having the same total area as the first surface.

As used herein, "insult point" refers to the first point where the urine stream from a wearer strikes the core of an absorbent article. Further, the expressions "male insult point" and "female insult point," as used herein, refer to the first point where the urine stream strikes the core of an absorbent article on a male and female wearer, respectively.

As used herein, the expression "absorbent article" refers to garments that absorb and contain exudates, and more specifically refers to articles that are placed against or in proximity to the body of the wearer to absorb and contain various exudates discharged from the body. A non-exhaustive list of examples of absorbent articles includes, but is not limited to, diapers, diaper cores, diaper covers, disposable diapers, training pants, feminine hygiene products and adult incontinence products. The expression "disposable article" refers to absorbent articles that are intended to be discarded or partially discarded after a single use, i.e., they are not intended to be laundered or otherwise restored or reused. The expression "unitary disposable absorbent article" refers to a disposable absorbent article that is essentially a single structure (i.e., it does not require separate manipulative parts such as a diaper cover and insert). As used herein, the term "diaper" refers to an absorbent article generally worn by infants and incontinent persons about the lower torso.

The claims are intended to cover all of the forgoing classes of absorbent articles, without limitation, whether disposable, unitary or otherwise. These classifications are used interchangeably throughout the specification, but are not intended to limit the claimed invention. The invention will be understood to encompass, without limitation, all classes of absorbent articles, including those described above. Preferably, the absorbent core is thin in order to improve the comfort and appearance of a garment. Employing thin, comfortable garments is disclosed, for example in U.S. Pat. No. 5,098,423 to Pineiak et al. which is herein incorporated by reference herein in its entirety.

The present invention is directed to particular core basis weight distributions that provide optimal absorbency. The cores of the absorbent articles, for the purposes of the invention, include any absorbent material in an absorbent article other than non-wovens and backsheets. Optionally, the core is a fibrous core. Further, the core is optionally comprised of pulp, a superabsorbent polymer (SAP), or combinations thereof.

The cores of the absorbent articles of the present invention optionally include a superabsorbent polymer (SAP) in an amount preferably ranging from about 10% to about 90% by weight of the total weight of the core, more preferably about 20% to about 80% by weight, and even more preferably 40% to 70% by weight. This SAP content may be uniform throughout the core, or the content may vary throughout the core. Preferably, the core has a pulp/SAP ratio which is substantial homogeneous, meaning that the SAP content is substantially uniform throughout the core.

Generally speaking, there are two schools of thought with regard to the design of absorbent articles. Under one school of thought, an absorbent article is designed so that the wicking ability of the core is such that fluid is pulled from the point of entry to the dry material so that the fluid is thus brought to the area of greatest absorbency. However, a second school of thought holds that it is better to tailor the absorbency to the site at which the fluid enters the absorbent article. The first concept results in lower efficiency cores, which in turn raises raw material costs. The second approach, however, is not so limited. The present invention provides absorbent articles, and methods for preparing same, in accordance with this second approach.

By way of theory, without being limited thereto, the benefit of having a high basis weight decreases as the basis weight is measured increasingly further from the point of insult in an absorbent article. In accordance with one implementation of the present invention, it is possible to characterize the basis weight distribution within an absorbent article. In one embodiment of this invention, a quantitative value may be determined that characterizes the basis weight distribution of the core in an absorbent article. This quantitative value can then be used as a design criteria for an absorbent article. In another implementation of the invention, the basis weight distribution of an absorbent article is characterized through an array of values that may be graphed in the form of a curve. The curve provides additional design parameters, based on factors such as breadth, flatness, and/or slope of the curve, without limitation.

According to one embodiment of the invention, an absorbent article is provided that includes a core characterized by a certain Distribution Index $_{i,j}$ ($DI_{i,j}$) at a determined point on the core of the absorbent article, or a core characterized by a Distribution Index profile. This Distribution Index or Distribution Index profile confers a desirable property or properties to an absorbent article, such as improved absorbency, fit, comfort, appearance, compatibility for males and females (e.g., for unisex use), longevity or a combination thereof, for example, without limitation.

In a further implementation of the invention, an absorbent article is provided that is characterized by a Distribution Index calculated according to general formula I, as follows:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \qquad (I)$$

wherein N is the total number of core cells of the core, each core cell of the core corresponding to each of a plurality of 0.75 inch squares on a predetermined grid;

wherein T is each positive integer from 1 to N, each said positive integer corresponding to each core cell of the core in numerical order;

wherein $DIST_T$ is a distance in centimeters (cm) between the center of the core cell corresponding to T and point i,j;

wherein $BW_T$ is the basis weight of each core cell, each said core cell corresponding to each value for T; and wherein i,j is a coordinate representing a point on the core.

According to another implementation of the invention, a certain Distribution Index $_{i,j}$ ($DI_{i,j}$) at a determined point on the core of the absorbent article, or a Distribution Index profile, is identified as conferring a desirable property to an absorbent article, such as improved absorbency, fit, comfort, appearance, compatibility for males and females, or a combination thereof, for example, without limitation. This DI or DI profile (a plurality of DI values corresponding to more than one point on the core) then is used as a design criteria for preparing improved cores and thus improved absorbent articles.

The DI for a core as used herein, that expression is determined according to the following methodology, referred to hereinafter as the Baker Method. First, the core of the absorbent article is divided into a plurality of sample cells, each cell being a discrete section on the absorbent article corresponding to a position on a grid. Then, an identifier, T (a positive integer ranging from 1 to the total number of sample cells, identified as N in general formula I), is assigned to each sample cell in the following manner, as illustrated in FIGS. 1, and 2A and 2B.

Referring to FIG. 1, a coordinate system is illustrated that shows the positioning of each of a plurality of points (i,j) on the core of an absorbent article. A Distribution Index may be calculated for any of the points on the core. Thus, the Distribution Index for a certain point on the core is denoted as Distribution Index$_{i,j}$ (DI$_{i,j}$). As shown in FIG. 1, the values for i indicate a distance (in cm) along the lengthwise direction of the core measured from the lengthwise fold of the absorbent article. As shown, at the fold, the value for i is 0. The values for i are positive values from the fold to the front of the article and negative values from the fold to the back of the article. As used herein, the front of the article corresponds to the front of a wearer of the absorbent article and the back of the article corresponds to the back of a wearer of the absorbent article. In FIG. 1, the front is shown on the right-hand side of the absorbent article. Likewise, the values for j indicate a distance (in cm) along the width of the core measured from the fold in the direction of the width of the core. The values for j are positive extending from the left of the centerline of the core and negative extending from the right of the centerline of the core, said left and right corresponding to the left side and the right side of the wearer, respectively. In FIG. 1, the left of the centerline is shown above the centerline. In this manner, the absorbency and other characteristics of various absorbent articles are compared by identifying and comparing the DI at certain points on the cores of absorbent articles. Further, an improved absorbent article can be designed by placing a certain DI at desired points on the core to achieve a desired effect.

Figure 2A:
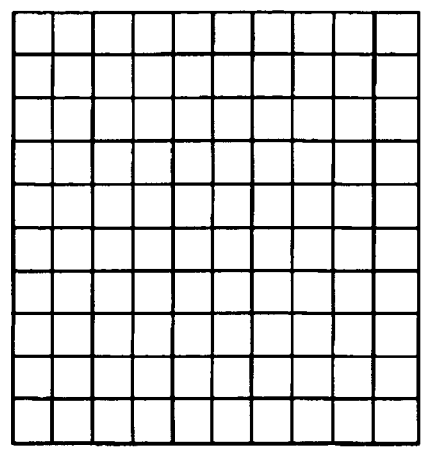
FIG. 2A is a pictorial representation of a grid used to measure the basis weight of an absorbent article in accordance with an embodiment of the invention.
Figure 2B:
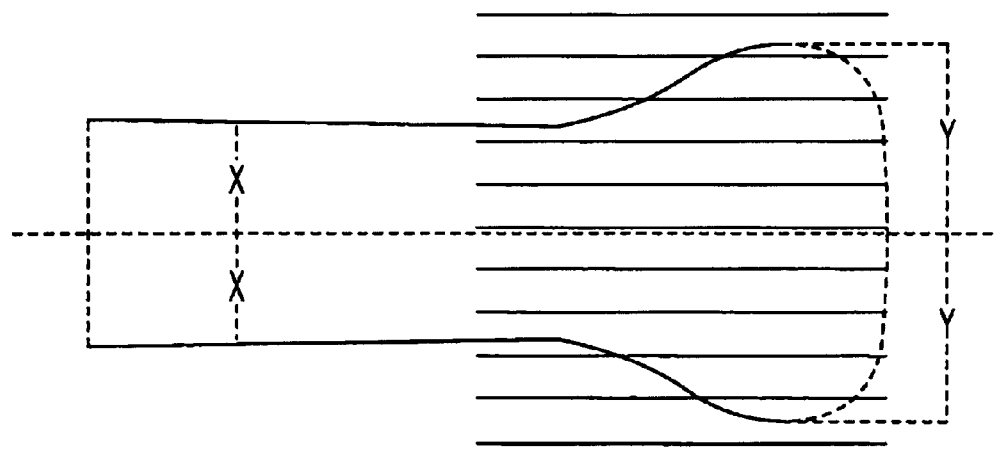
FIG. 2B is a pictorial representation of the grid as it corresponds to an absorbent article and core thereof.

Referring to FIGS. 2A and 2B, for the purposes of determining the DI, a sample must first be prepared. For example, where the absorbing article is a diaper, the sample is prepared as follows. First, the diaper is opened flat with the topsheet up. Then, the inner leg gathers are carefully removed without making tears in the topsheet. Next, in such a manner as not to disrupt the core or create holes from which SAP can spill, the leg gathers are cut away so that the core of the diaper will lay flat. At the front of the diaper, the width of the diaper core is measured and the center point is determined and marked with a tick mark. This measurement is then repeated at the rear of the diaper. A line is then drawn on the diaper that connects these tick marks. This line is referred to as the centerline. In this manner, a sample is prepared which is then available for subsequent testing.

The DI for a point on a sample of an absorbent article is then tested in the following manner, according to the Baker Method. The front of the sample is placed on a steel rule die grid, as shown in FIG. 2B. The centerline of the sample is aligned with the center blade of the die grid. The center blade then is marked with tick marks and an arrow pointing toward the front direction. Then, the die containing the sample is placed on a USM Platten die press machine such that the sample is facing up. A small stack of about 10 sheets of paper is placed on top of the sample and a plastic cutting board is placed over the sheets of paper. It is preferred to ensure that the plastic cutting board covers all blades of the die. A clean and thorough cut then is made into the sample using the USM Platten die press machine. The cut paper must then be carefully removed without disrupting the topsheets on each of a plurality of sample cells that have been formed by the cut, each said sample cell corresponding to each discrete square section on the grid. Being careful not to spill any of the SAP, the remaining intact sample is set aside for later use. An arrow is drawn on the sample to indicate the forward direction. A 10 inch by 10 inch likeness of the die is drawn on grid paper, leaving ample space for writing 3 lines of measurement for each sample cell. The measurements are then recorded on a paper that has been pre-labeled with the grid coordinates.

Using a knife, a first square of the sample is carefully removed from the die and weighed to the nearest 0.001 gram. This weight then is recorded on the first line in the grid square corresponding to the sample cell. Next, all non-wovens, backsheets and topsheet are removed from the scale. The weight then is measured again and recorded on the second line in the corresponding grid square. If the core portion of the square is smaller than the 0.75 inch by 0.75 inch cut, the average width and average height to the nearest millimeter (which allows calculation of the area of the remaining piece) of the core is measured with electronic calipers (in mm). These measurements then are recorded on the third line in the corresponding grid square. The sample cell that has just been measured then is discarded and each of the remaining sample cells is treated in the same manner as the first data cell. Once the entire die has been measured and recorded, an annotation is made regarding the portion of the absorbent article that was measured on the top of the grid sheet (i.e. front, middle, back). The above procedure then is repeated until the entire core has been cut, weighed and recorded.

The basis weight for each cell then is determined according to general formula II or general formula III. In particular, for all cells where the core completely covers the entire 0.75 inch×0.75 inch square area of the cell, the basis weight is calculated using general formula II, as follows:

$$BW_T\left(\frac{g}{m^2}\right) = \frac{SampleWeight_T(g) - SurroundsWeight_T(g)}{0.003629(m^2)} \quad (II)$$

Alternatively, for all cells where the core does not completely cover the entire 0.75×0.75 inch square area of the cell, the basis weight is calculated using general formula III.

$$BW_T\left(\frac{g}{m^2}\right) = \frac{SampleWeight_T(g) - SurroundsWeight_T(g)}{width(mm) * length(mm)} \left(\frac{100(mm)}{m}\right)^2 \quad (III)$$

As used herein, the term "SampleWeight$_T$" refers to the weight of each sample cell. "SurroundsWeight$_T$", as used herein, refers to the weight of the backsheet, topsheet and other non-wovens that are not part of the core for each sample cell. The weight may be determined by using a scale, a balance or any such means.

Accordingly, in the above manner, the basis weight for each core cell (i.e., each discrete square section of the core corresponding to each sample cell), as designated as BW$_T$, is determined. The basis weight for each core cell BW$_T$, calculated using general formulas (II) or (III), as described above, then is used in general formula (I) for calculating the DI of the core of the absorbent article at a particular point.

The DI is thus finally determined by using the following general formula:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

wherein N is the total number of core cells of the core, each core cell of the core corresponding to each of a plurality of 0.75 inch squares on a predetermined grid;

wherein T is each positive integer from 1 to N, each positive integer corresponding to each core cell of the core in numerical order;

wherein DIST$_T$ is a distance in centimeters (cm) between the center of the core cell corresponding to T and point i,j;

wherein BW$_T$ is the basis weight of each core cell, each core cell corresponding to each value for T; and wherein i,j is a coordinate representing a point on the core.

Figure 5:
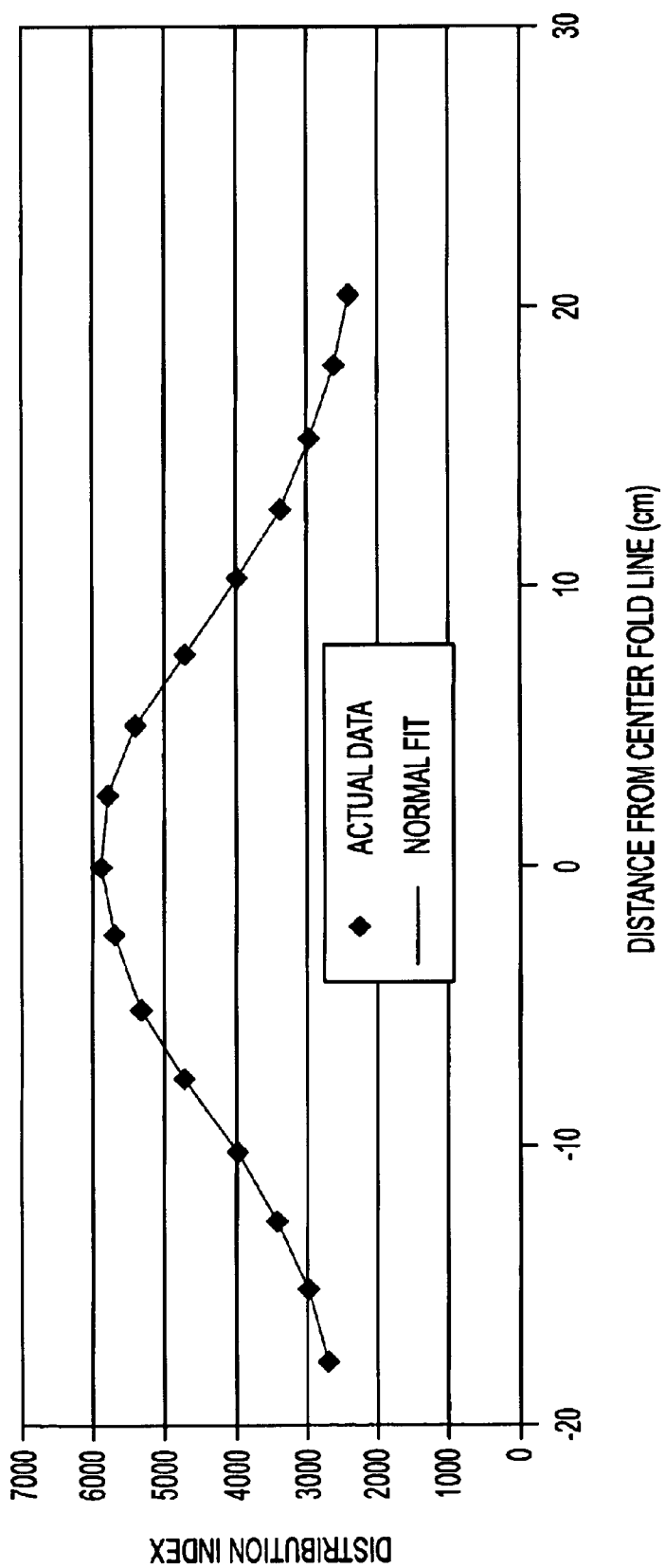
FIG. 5 is a graph illustrating a Distribution Index profile when fitted to a gaussian equation.

$BW_T$ can be determined using any conventional means as would be well known to persons of ordinary skill in the art, using the guidelines provided herein. Accordingly, a DI for any point on the core of an absorbent article is determined. The DI values obtained in the above manner have a wide range of uses. For example, a graphical representation of the absorbent article's DI values may be developed (e.g., a DI profile as shown in FIG. 5) and compared to the graphical representation of other absorbent articles, without limitation. Further, for example, a $DI_{max}$, $DI_{layerage}$, $DI_{male}$, $DI_{female}$, a DI at any desired point, or other such values may be determined and compared to the corresponding values of other absorbent articles, without limitation.

Any conventional methods and/or any conventional materials, as known to persons of ordinary skill in the art may be incorporated into various embodiments of the present invention. In particular, cores having a desirable DI profile, DI at a certain point (e.g., at the male or female insult point, without limitation), $DI_{max}$, $DI_{min}$ or combination thereof, may be prepared using conventional methods that are readily known and available to persons of ordinary skill in the art, in combination with the technique for determining a Distribution Index (DI) described and claimed herein.

Absorbency distribution in absorbent articles may be compared through a comparison of various DIs, the various DIs include, for example, DIs measured at comparative points i,j on two or more cores, the maximum distribution index ($DI_{max}$) on the cores, the minimum distribution index ($DI_{min}$), the average distribution index ($DI_{average}$), the distribution index at a point or a plurality of points on the cores, DI profiles or combinations thereof, without limitation. The DI for a plurality of points on a core can form a distribution index profile which is compared to the DI profile corresponding to the same plurality of points on another core. In this manner, various product brands may be compared to one another.

For example, a higher DI at a certain point on the core, indicates that the greater proportion of absorbent capacity is closer to the insult point (i.e., the point at which fluid enters the core). Accordingly, the higher DI at a certain point or at a plurality of points, relative to the DI at other points, confers advantages in terms of absorbent efficiency, as well as cost efficiency.

Figure 3:
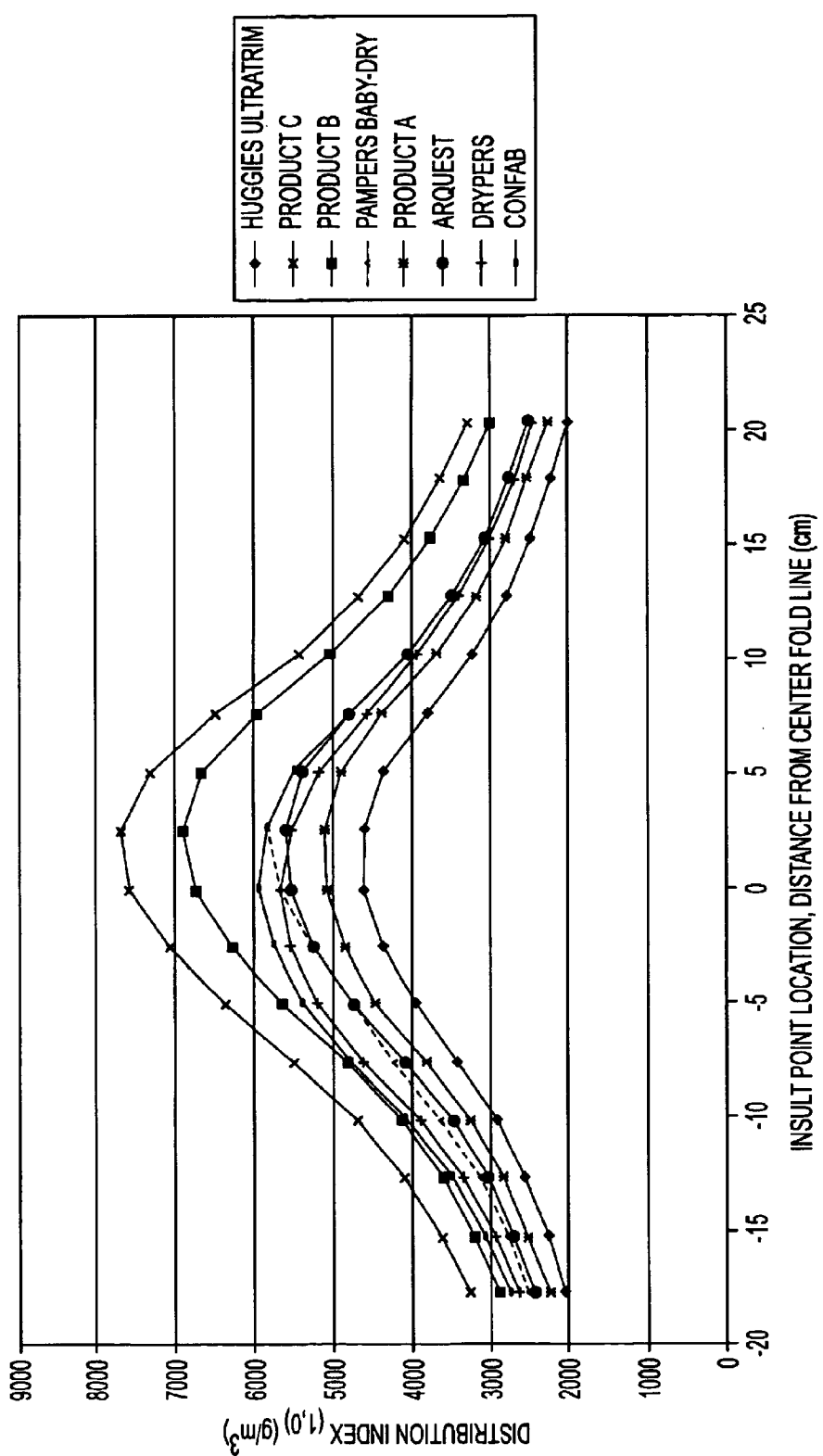
FIG. 3 is a graph comparing the Distribution Index profiles of the cores of various diaper brands as determined in a repeatability study.

Table I is the result of a study performed on various product brands for the purpose of comparing the DIs at various points along the centerline (where j is 0) of each core. In total, eight product brands were tested in the study. As Table I shows, a DI profile may be determined for each of the product brands. A comparison of the DI profile for each brand is illustrated in FIG. 3. As shown in FIG. 3, the DI profile forms a curve that provides a useful comparison between product brands.

Referring again to FIG. 3, Product A, Product B, and Product C, in accordance with embodiments of the present invention, have DI profile curves that are substantially distinct from the DI profile curves of the competing brands that were tested. In particular, Products B and C have substantially higher values for $DI_{max}$ as well as substantially higher DI values measured at a plurality of other points along the centerline of the core, and particularly those points closest to the insult point of the core. Accordingly, the DI profile distinguishes products having superior absorbency efficiency and/or cost efficiency. Moreover, it would be well within the skill of the art, in view of the disclosure herein, to prepare an absorbent article having a core which conforms to a predetermined DI profile that is identified as conferring a superior performance characteristic or characteristics.

TABLE I

| | Product/Brand Distribution Index (DI) | | | | | | | |
|---|---|---|---|---|---|---|---|---|
| Centerline Distance | Huggies Ultratrim | Product A | Product B | Pampers Baby-Dry | Product C | Arquest Dry-bottoms | Drypers | Confab |
| 20.32 | 1941 | 2210 | 2964 | 2444 | 3251 | 2409 | 2380 | 2474 |
| 17.78 | 2151 | 2452 | 3297 | 2712 | 3611 | 2675 | 2633 | 2736 |
| 15.24 | 2413 | 2756 | 3715 | 3049 | 4062 | 3008 | 2947 | 3062 |
| 12.70 | 2749 | 3147 | 4259 | 3483 | 4646 | 3437 | 3348 | 3480 |
| 10.16 | 3191 | 3668 | 4990 | 4064 | 5429 | 4008 | 3876 | 4035 |
| 7.62 | 3766 | 4348 | 5960 | 4842 | 6471 | 4754 | 4548 | 4777 |
| 5.08 | 4310 | 4884 | 6663 | 5528 | 7313 | 5365 | 5155 | 5462 |
| 2.54 | 4584 | 5098 | 6894 | 5819 | 7681 | 5573 | 5519 | 5828 |
| 0.00 | 4592 | 5062 | 6742 | 5701 | 7578 | 5520 | 5646 | 5920 |
| −2.54 | 4340 | 4850 | 6289 | 5266 | 7062 | 5240 | 5537 | 5735 |
| −5.08 | 3936 | 4450 | 5641 | 4721 | 6381 | 4732 | 5206 | 5372 |
| −7.62 | 3419 | 3829 | 4810 | 4188 | 5508 | 4082 | 4619 | 4781 |
| −10.16 | 2919 | 3262 | 4124 | 3622 | 4703 | 3488 | 3908 | 4062 |
| −12.70 | 2540 | 2839 | 3609 | 3147 | 4102 | 3042 | 3367 | 3499 |
| −15.24 | 2249 | 2515 | 3211 | 2785 | 3639 | 2699 | 2960 | 3076 |
| −17.78 | 2019 | 2259 | 2894 | 2499 | 3273 | 2427 | 2643 | 2746 |

Figure 4:
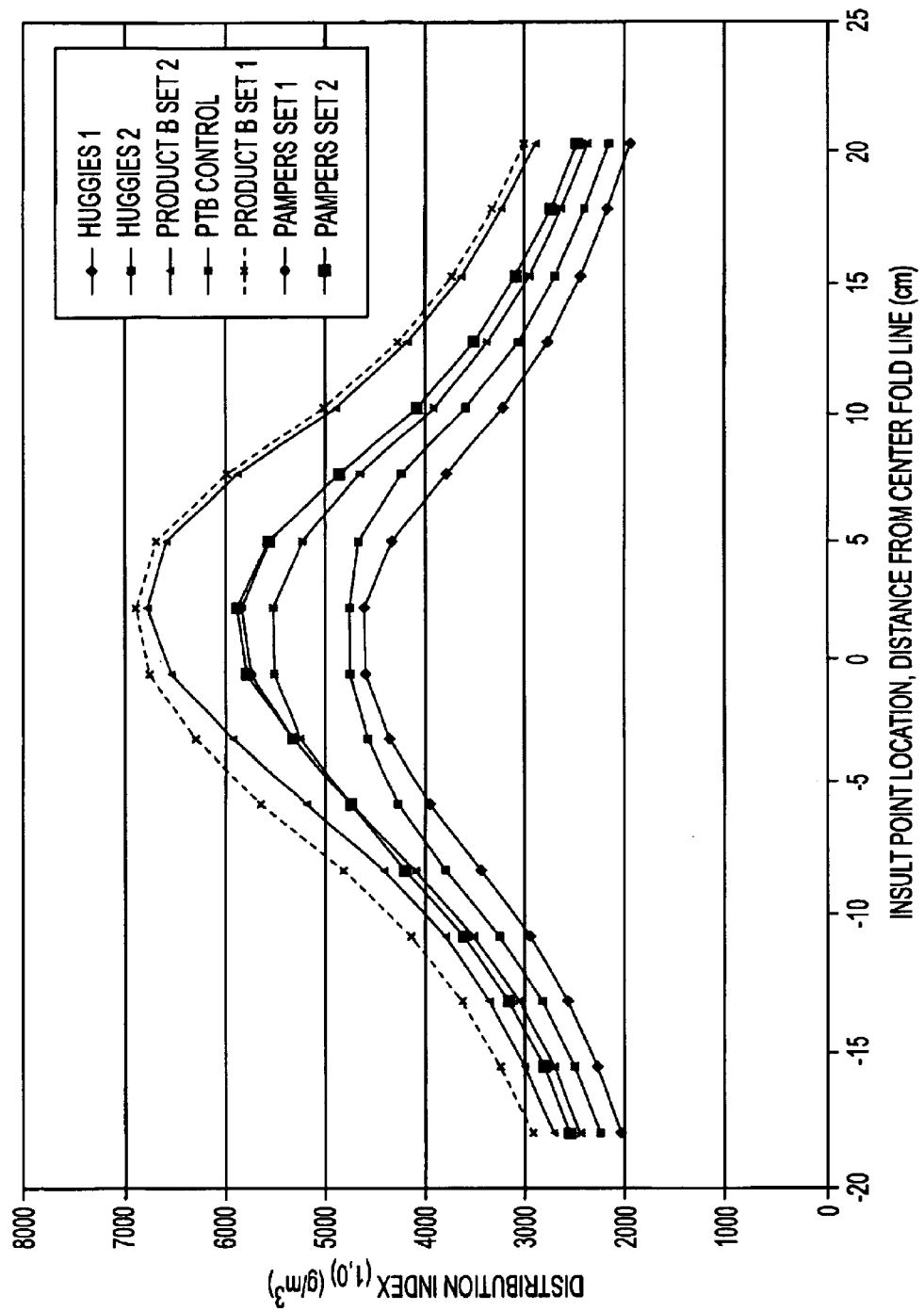
FIG. 4 is a graph comparing the Distribution Index profiles of the cores of various diaper brands.

Table II shows a repeatability study for various product brands. As in Table I described above, Table II shows the results of a study performed on various product brands for the purpose of comparing the DIs at various points along the centerline (where j is 0) of each core. In total, three product brands were tested in the study. As Table II shows, a DI profile was determined for each of the product brands. A comparison of the DI profile for each brand in the repeatability study is illustrated in FIG. 4. As shown in FIG. 4, the DI profile forms a curve that provides a useful comparison between the product brands.

TABLE II

Distribution Index Repeatability Study

| Position (i) | Huggies Ultratrim | Huggies Ultratrim | Pampers Baby-Dry | Pampers Baby-Dry | Product B | Product B |
|---|---|---|---|---|---|---|
| 20.32 | 1941 | 2138 | 2444 | 2457 | 2964 | 2877 |
| 17.78 | 2151 | 2375 | 2712 | 2727 | 3297 | 3205 |
| 15.24 | 2413 | 2673 | 3049 | 3065 | 3715 | 3619 |
| 12.70 | 2749 | 3059 | 3483 | 3501 | 4259 | 4159 |
| 10.16 | 3191 | 3573 | 4064 | 4084 | 4990 | 4889 |
| 7.62 | 3766 | 4230 | 4842 | 4859 | 5960 | 5867 |
| 5.08 | 4310 | 4636 | 5528 | 5551 | 6663 | 6567 |
| 2.54 | 4584 | 4738 | 5819 | 5883 | 6894 | 6766 |
| 0.00 | 4592 | 4708 | 5701 | 5778 | 6742 | 6529 |
| −2.54 | 4340 | 4565 | 5266 | 5307 | 6289 | 5910 |
| −5.08 | 3936 | 4241 | 4721 | 4742 | 5641 | 5159 |
| −7.62 | 3419 | 3767 | 4188 | 4195 | 4810 | 4383 |
| −10.16 | 2919 | 3222 | 3622 | 3624 | 4124 | 3783 |
| −12.70 | 2540 | 2794 | 3147 | 3151 | 3609 | 3330 |
| −15.24 | 2249 | 2468 | 2785 | 2790 | 3211 | 2975 |
| −17.78 | 2019 | 2211 | 2499 | 2505 | 2894 | 2690 |

Table III shows the $DI_{average}$ for various product brands. The DI average represents an average of the DI values for selected insult points along the centerline of the core. Specifically, this is the average of all the DI values for insult points calculated along the centerline of the core at one inch intervals. The DI average is substantially higher for Products A and B, when compared to the other product brands, as shown in Table III. This substantially higher DI average corresponds to higher absorbency efficiency and improved cost efficiency. Accordingly, DI average values are useful as designed parameters for cores in absorbent articles. In one embodiment of the present invention, an absorbent article is provided that has a core having a $DI_{average}$ of at least about 4,500 grams per cubic meter, preferably at least about 4,750 grams per cubic meter, more preferably about 5,000 grams per cubic meter and even more preferably at least about 5,500 grams per cubic meter.

TABLE III

| | Average DI across centerline | | |
|---|---|---|---|
| Product Type | rep 1 | rep 2 | avg. |
| Huggies | 3195.0 | 3462.4 | 3328.7 |
| Product A | 5294.4 | | 5294.4 |
| Product B | 4753.9 | 4544.2 | 4649.1 |
| Pampers baby-dry | 3991.9 | 4013.7 | 4002.8 |
| Product C | 3601.9 | 3858.4 | 3730.1 |
| Arquest Drybottoms | 3909.7 | | |
| Drypers | 4018.3 | | |
| Confab | 4190.3 | | |

In one embodiment of the invention a DI profile may be fitted to the gaussian equation of formula IV:

$$Y = Y_0 + ae^{\left[-.5\left(\frac{x-x_0}{b}\right)^2\right]} \quad \text{(IV)}$$

where $x_0$ is the distance along the midline corresponding to $DI_{max}$; a is the $DI_{average}$; b is the standard deviation of the curve; Y is the distribution index at a certain point; x is the distance at a certain point along the centerline; $Y_0$ is $DI_{min}$.

Table IV shows values for $Y_0$, a, b, and $x_0$ for various product brands. The $Y_0$ value is significant because a low $DI_{min}$ equates to a higher level of costs efficiency, while there is a floor beneath which the $DI_{min}$ should not drop because a $DI_{min}$ that is too low would result in absorbency problems, particularly for babies sleeping on their backs. Accordingly, there is an optimal $DI_{min}$ that provides the maximum amount of cost effectiveness that can be obtained by minimizing absorbency in the back of the diaper while not minimizing the absorbency to so great an amount that the core would not meet minimal performance demands. Preferably, the $DI_{min}$ of the core of an absorbent article is about 2,800 to about 3,600 grams per cubic meter, more preferably about 2,900 grams per cubic meter to about 3,300 grams per cubic meter, and even more preferably about 2,950 grams per cubic meter to about 3,200 grams per cubic meter. Exemplary data from Table IV is shown in the graph in FIG. 5 as a curve defined by a gaussian equation, as described above. As shown in the graph, the gaussian curve closely fits the Distribution Index profile curve. Accordingly, the present invention contemplates identifying DI profiles represented as a guassian equation corresponding to a gaussian curve of a plurality of plotted DI points along a core. In this manner, it is possible to obtain gaussian equations that define a desirable absorbency profile. This equation can be used for comparison to other cores or can be used as a design parameter in forming cores having one or more desired characteristics.

TABLE IV

| | Product/Brand DI | | | | | | |
|---|---|---|---|---|---|---|---|
| | Product A | Huggies | Pampers | Product B | Arquest | Drypers | Confab |
| $y_0$ | 2745.1 | 1836.0 | 2332.6 | 2029.4 | 2207.0 | 2207.0 | 2300.8 |
| a | 4163.3 | 2979.5 | 3441.1 | 3122.7 | 3483.1 | 3483.1 | 3657.4 |

TABLE IV-continued

| | Product/Brand DI | | | | | | |
|---|---|---|---|---|---|---|---|
| | Product A | Huggies | Pampers | Product B | Arquest | Drypers | Confab |
| b | 7.9 | 9.1 | 7.9 | 8.3 | 8.1 | 8.6 | 8.5 |
| $x_0$ | 1.7 | 1.0 | 1.3 | 1.0 | 1.3 | −0.1 | 0.0 |

In another implementation of the invention, an absorbent article is provided having a core with a certain DI for male babies ($DI_{male}$) and/or a certain DI for female babies ($DI_{female}$), or ranges thereof, to provide superior characteristics. In a further implementation of the invention, an absorbent article is provided that has a DI profile such that the difference between the values for $DI_{male}$ and $DI_{female}$ is within a certain range. In this manner, a core may be provided that is optimal for both male and female use (e.g., unisex use).

Table V shows various parameters for male and female babies that participated in a study to determine the site of the male and female insult points. For example, the male insult point was determined to be 12 cm from the top of the core, and the female insult point was determined to be 16 cm from the top of the core. The insult points for both males and females will vary according to the age of the baby. As used herein, male, insult points and female insult points are both intended to be age specific terms. Therefore, the male insult point and the female insult point needs to be determined for each particular absorbent article being tested. However, this may be accomplished through conventional methods well known to persons of skill in the art.

TABLE V

| | Average | | | Standard Deviation | | |
|---|---|---|---|---|---|---|
| | Male | Female | p = | Male | Female | p = |
| Weight (lbs) | 27.7 | 24.8 | 0.04 | 3.2 | 2.8 | 0.65 |
| Waist (mm) | 461 | 437 | 0.28 | 12 | 55 | 0.00 |
| Thigh left (mm) | 275 | 255 | 0.29 | 28 | 45 | 0.24 |
| Thigh Right (mm) | 273 | 253 | 0.14 | 26 | 32 | 0.63 |
| Hip to Hip (mm) | 185 | 177 | 0.42 | 20 | 25 | 0.62 |
| Hip to ground (mm) | 398 | 405 | 056 | 15 | 30 | 0.09 |
| Initial Tab—Tab (mm) | 87 | 76 | 0.20 | 18 | 19 | 0.99 |
| Used Tab—Tab (mm) | 83 | 73 | 0.12 | 17 | 13 | 0.34 |

Table VI shows the results of the study to determine the $DI_{male}$ and $DI_{female}$ for various product brands. Also shown in Table VI is the difference between the values measured for $DI_{male}$ and $DI_{female}$ for each of those competing product brands. As shown in the Table, the difference between the $DI_{male}$ and $DI_{female}$ for the Huggies 2 brand is the lowest value. However, the difference between the $DI_{male}$ and $DI_{female}$ in the Huggies 2 brand is still 1045 grams per cubic meter. This is a substantial difference when considering a unisex product. By minimizing this difference, a product of superior absorbent characteristics as well as superior cost efficiency is provided, in accordance with one embodiment of the invention. Preferably, the difference between the $DI_{male}$ and $DI_{female}$ is at most about 1,000 grams per cubic meter, more preferably the difference between the $DI_{male}$ and $DI_{female}$ is at most about 900 grams per cubic meter, even more preferably the difference between the $DI_{male}$ and $DI_{female}$ is at most about 600 grams per cubic meter, and even more preferably the difference between the $DI_{male}$ and $DI_{female}$ is at most about 400 grams per cubic meter, and most preferably the $DI_{male}$ and $DI_{female}$ are substantially the same. Further, the $DI_{male}$ and $DI_{female}$ are preferably at least about 4,200 grams per cubic meter and at least about 5,500 grams per cubic meter, respectively. More preferably, the $DI_{male}$ and $DI_{female}$ are each at least about 4,500 grams per cubic meter.

TABLE VI

| | Male | Female | Diff |
|---|---|---|---|
| Huggies Ultratrim | 3163 | 4317 | 1054 |
| Huggies 2 | 3541 | 4586 | 1045 |
| Pampers Baby-Dry | 4027 | 5416 | 1388 |
| Pampers2 | 4047 | 5437 | 1390 |
| Arquest DryBottoms | 3972 | 5275 | 1303 |
| Drypers | 3843 | 5047 | 1204 |
| Confab | 4000 | 5348 | 1348 |
| Insult Point (x = 0) | 10.3 | 5.6 | |

Figure 6:
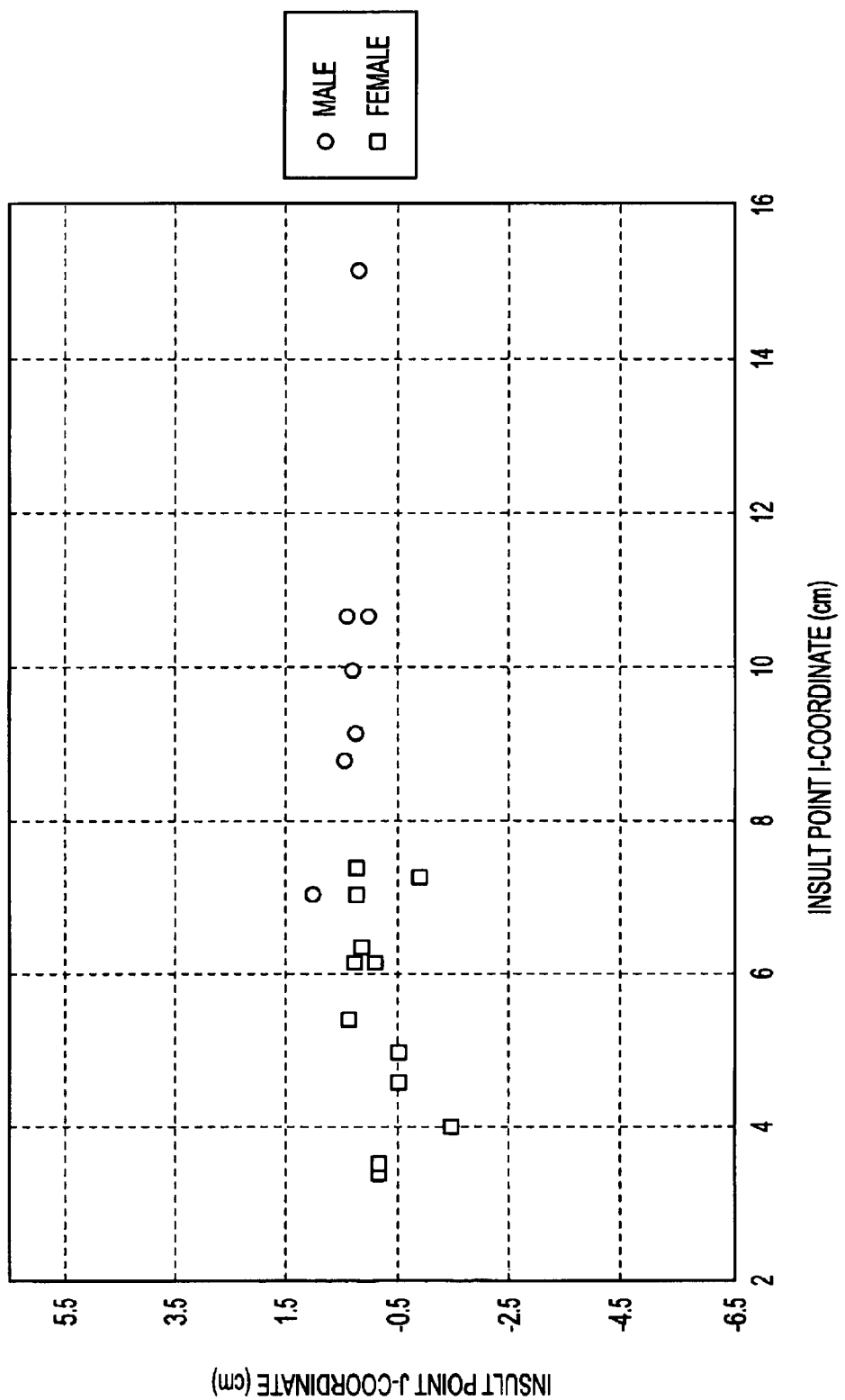
FIG. 6 is a graph illustrating insult points on diaper brands in a gender-based study.
Figure 7:
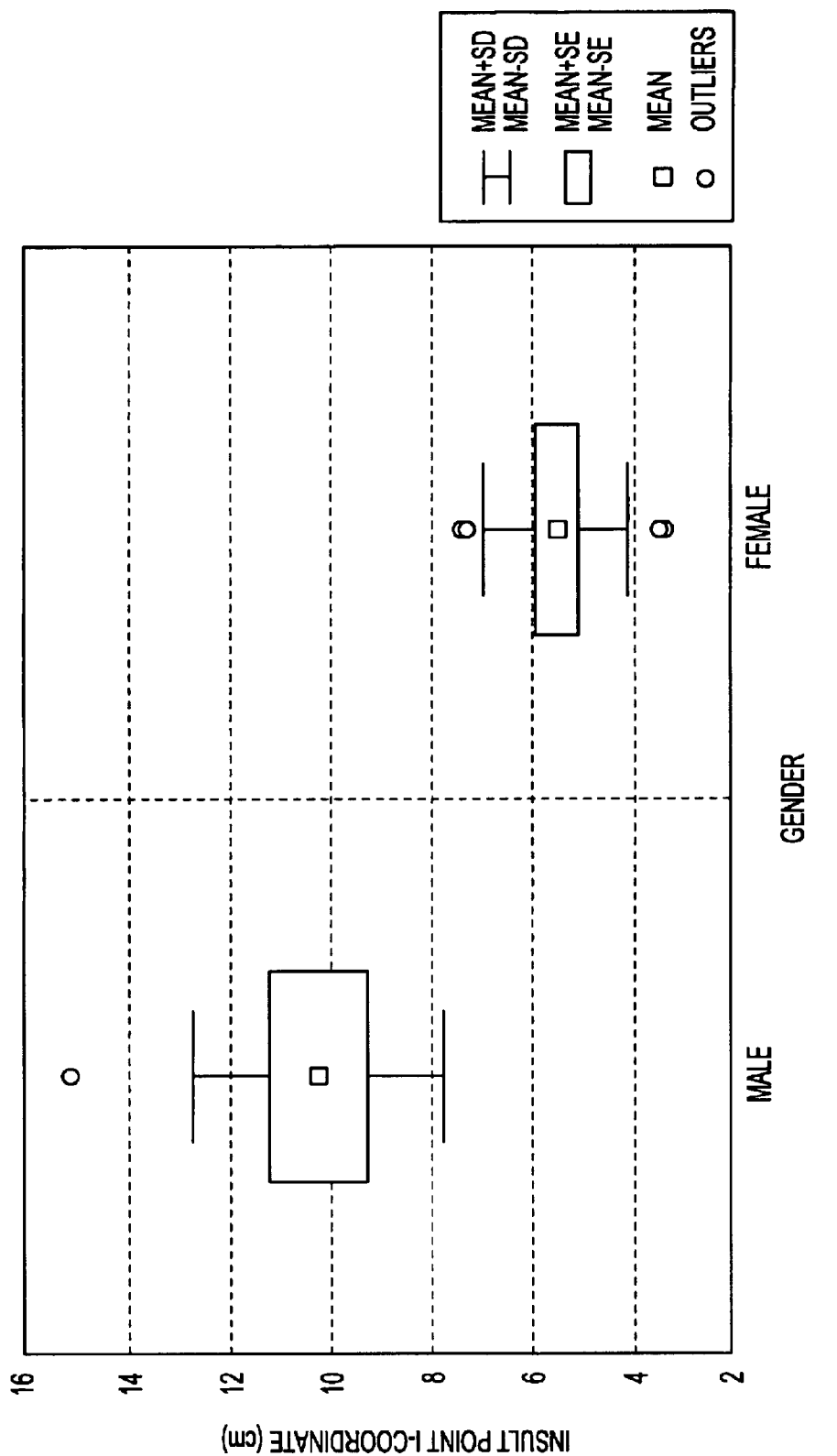
FIG. 7 is a graph illustrating insult points on diaper brands in a gender-based statistical study.
Figure 8:
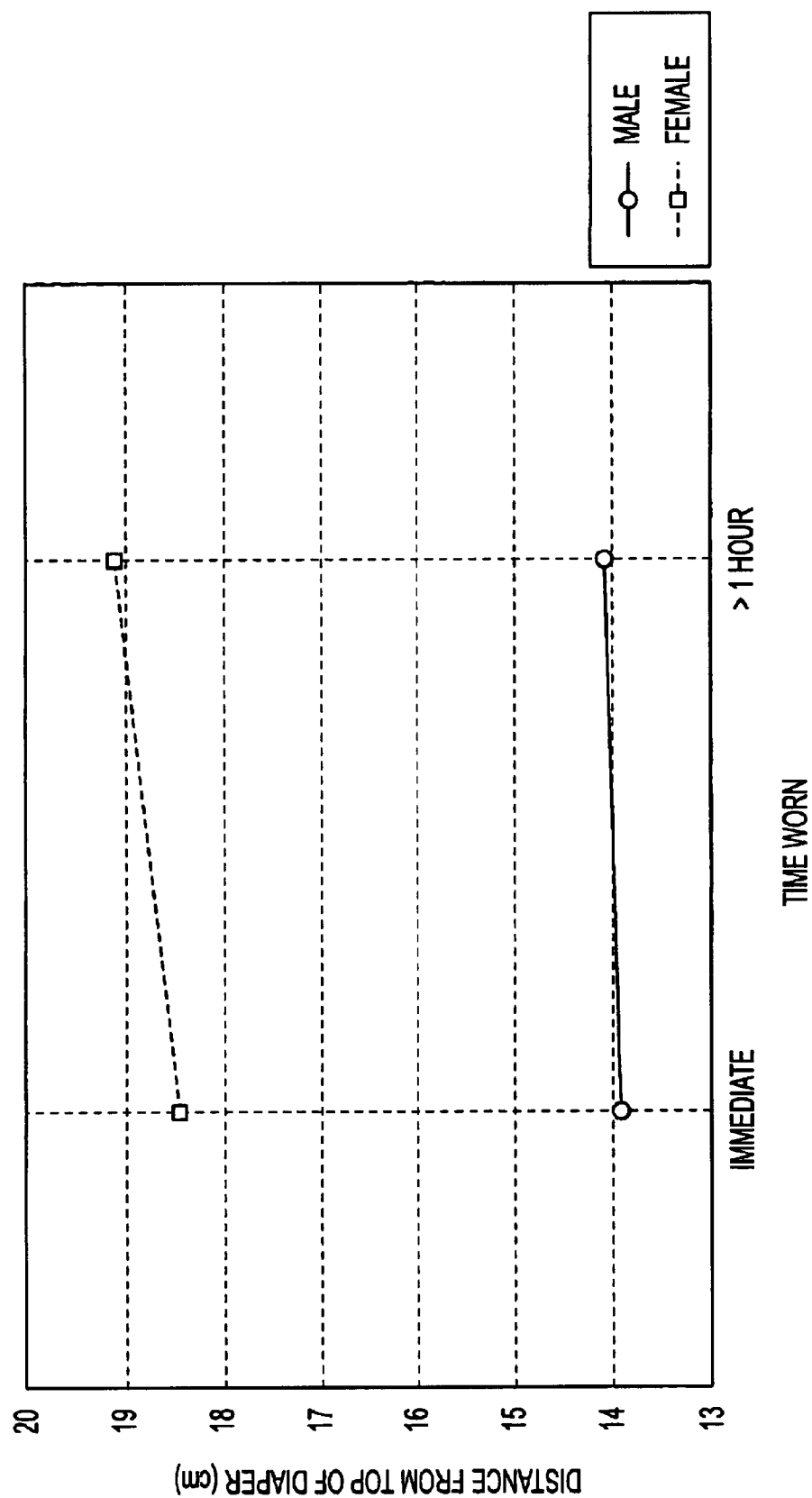
FIG. 8 is a graph illustrating variation in insult point over time in a gender-based study.

FIGS. 6, 7 and 8 show graphs that illustrate the results from the study to determine the site of insult points for male and female babies. In particular, FIG. 6 shows various insult points by gender as a function of distance from the top of the core and distance from the centerline along the core.

FIG. 7 shows the results of the insult points study for male and female babies as a function of gender and distance from the diaper fold in centimeters (cm). As shown in the figure, the male insult points are on average about 10.3 cm from the fold (where i,j is 0,0) of the diaper and the female insult points are on average about 5.6 cm from the fold of the diaper. Moreover, according to the study, male insult points are more variable than female insult points. This is shown in the figure by the standard deviation for males which equals about 2.5 cm as opposed to the standard deviation for females, which equals about 1.5 cm. A diaper having a substantially similar absorbency at the male and female insult points is obtained in accordance with one implementation of the invention. In particular, a core may be formed having a DI index at the male and female insult points which is substantially similar, as described above. In this manner, the present invention provides a superior unisex diaper (e.g., a diaper which is optimal for males and females). As used herein male insult point refers to average male insult point and female insult point refers to average female insult point. Persons of ordinary skill in the art appreciate that the insult point will vary as a function of age of the child. Accordingly, the present invention contemplates adjustments to tailor the absorbent article to children of different ages, which is well within the skill of the art.

FIG. 8 shows the results of the insult points study for males and females with regard to variations and insult points over time. The graph in FIG. 8 shows the changes in insult point as a function of time and distance from the top of the diaper (cm). As the graph illustrates, over time the insult point appears to move up. This is likely due to sagging of the diaper.

In accordance with an implementation of the invention, changes in position of the insult point caused by sagging can be accounted for by tailoring a Distribution Index Profile of an absorbent article in accordance with the known change in position of the insult points that occur when the diaper begins sagging. In particular, the DI may be substantially similar in the area around and between the original insult point and the post-sagging insult point. Thus, absorbency is provided in the areas of greatest need during the course of use of the diaper by the wearer. In this manner, an absorbent article having superior longevity may be provided by the present invention. This would be particularly useful, for example, for an extended-use diaper, a nighttime diaper (e.g., a diaper intended primarily for use during the nighttime) and/or a travel diaper (e.g., a diaper intended primary for use during travel or a long road trip, or during any somewhat long period of time during which changing the diaper would be generally inconvenient), without limitation.

Due to the wide variety of materials that may be incorporated into the absorbent articles of the present invention, the invention is not intended to be limited to any specific materials. Non-limiting exemplary fibers that may be included in the article and or process of the present invention include, without limitation, cellulose fibers, cellulose acetate fibers, rayon fibers, Courtauld's LYOCEL fibers, polyacrylonitrile fibers, surface modified (hydrophilic) polyester fibers, surface modified polyolophin/polyester by component fibers, surface modified polyester/polyester bicomponent fibers, cotton fibers or blends thereof. Preferably cellulose acetate, rayon, Courtauld's LYOCEL, polyacrylonitrile, cotton fibers and cotton linters or combinations thereof are used in the process of the present invention. More preferably, cellulose fibers are used as the fiber material in the present invention. Other materials may be added to the fiber or pulp material that is processed in the hammermill. The additives may be added at any point in the process.

Preferably, the additives are sprayed or injected into the airborne fibers prior to depositing the fibers on the forming surface. Non-limiting exemplary additives that may be incorporated into the process of the present invention include a polymer such as a SAP, hydrophilic polymers, potato starch, corn starch, wheat starch or rice starch, or combinations thereof. Various different combinations of materials may be used as are known to persons of ordinary skill in the art and that are described in U.S. Pat. No. 6,068,620, which is herein incorporated by reference in its entirety.

The following examples are illustrative of preferred embodiments of the inventive subject matter and are not to be construed as limiting the inventive subject matter thereto.

EXAMPLE I

Absorbent Articles having an Improved Core

The following Distribution Index $_{i,j}$ ($DI_{i,j}$) values may be used to prepare cores of absorbent articles in accordance with an implementation of the present invention:

TABLE VII

| Centerline Distance (cm) I | SAP Content by Weight | Distribution Index (Di(i,o)(g/m³) |
|---|---|---|
| 20.32 | about 10%–90% | at least about 2900 |
| 17.78 | about 10%–90% | at least about 3200 |
| 15.24 | about 10%–90% | at least about 3700 |
| 12.70 | about 10%–90% | at least about 4200 |
| 10.16 | about 10%–90% | at least about 4900 |

TABLE VII-continued

| Centerline Distance (cm) I | SAP Content by Weight | Distribution Index (Di(i,o)(g/m³) |
|---|---|---|
| 7.62 | about 10%–90% | at least about 5900 |
| 5.08 | about 10%–90% | at least about 6660 |
| 2.54 | about 10%–90% | at least about 6890 |
| 0.00 | about 10%–90% | at least about 6700 |
| -2.54 | about 10%–90% | at least about 6250 |
| -5.08 | about 10%–90% | at least about 5600 |
| -7.62 | about 10%–90% | at least about 4800 |
| -10.16 | about 10%–90% | at least about 4100 |
| -12.70 | about 10%–90% | at least about 3600 |
| -15.24 | about 10%–90% | at least about 3200 |
| -17.78 | about 10%–90% | at least about 2850 |

The cores characterized by the above DI values are prepared using conventional methods and materials. These methods and materials are well known to persons of ordinary skill in the art, using the guidelines provided herein. It would be well within the skill of the art to prepare absorbent articles having the parameters disclosed and claimed herein.

EXAMPLE II

Diaper having an Improved Core

The following Distribution Index $_{i,j}$ ($DI_{i,j}$) values may be used to prepare cores of diapers in accordance with an implementation of the present invention:

TABLE VIII

| Centerline Distance (cm) I | SAP Content by Weight | Distribution Index (DI)(g/m³) |
|---|---|---|
| 20.32 | about 70% | about 3251 |
| 17.78 | about 70% | about 3611 |
| 15.24 | about 70% | about 4062 |
| 12.70 | about 70% | about 4646 |
| 10.16 | about 70% | about 5429 |
| 7.62 | about 70% | about 6471 |
| 5.08 | about 70% | about 7313 |
| 2.54 | about 70% | about 7681 |
| 0.00 | about 70% | about 7578 |
| -2.54 | about 70% | about 7062 |
| -5.08 | about 70% | about 6381 |
| -7.62 | about 70% | about 5508 |
| -10.16 | about 70% | about 4703 |
| -12.70 | about 70% | about 4102 |
| -15.24 | about 70% | about 3639 |
| -17.78 | about 70% | about 3273 |

The cores characterized by the above DI profiles are prepared using conventional methods and materials well known to persons of ordinary skill in the art, using the guidelines provided herein.

The invention has been described in connection with the preferred embodiments. These embodiments, however, are merely for example and the invention is not restricted thereto. It will be understood by those skilled in the art that other variations and modifications can easily be made within the scope of the invention as defined by the appended claims.

What is claimed is:

1. An absorbent article comprising:
   a core comprised of pulp, a polymer or a combination thereof;
   wherein the core has a maximum Distribution Index ($DI_{max}$) of at least about 6,000 g/m3; and
   wherein the $DI_{max}$ is the maximum DI(i,j,) value on said absorbent article, said ($DI_{i,j}$) being determined according to Formula I:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

by using the Baker Method.

2. The absorbent article of claim 1, wherein the $DI_{max}$ is at least about 6,500 g/m³.

3. The absorbent article of claim 1, wherein the $DI_{max}$ is at least about 7,000 g/m³.

4. The absorbent article of claim 1, wherein the $DI_{max}$ is at least about 7,500 g/m³.

5. The absorbent article of claim 1, wherein the core is comprised of about 10% to about 90% by weight of particulate or fibrous SAP.

6. The absorbent article of claim 1, wherein the core is comprised of about 20% to about 80% by weight of particulate or fibrous SAP.

7. The absorbent article of claim 1, wherein the core is comprised of about 40% to about 70% by weight of particulate or fibrous SAP.

8. The absorbent article of claim 1, wherein the core has a minimum Distribution Index ($DI_{min}$) of about 2,800 g/m³ to about 3,600 g/m³.

9. The absorbent article of claim 1, wherein the core has a minimum Distribution Index ($DI_{min}$) of about 2,900 g/m³ to about 3,300 g/m³.

10. The absorbent article of claim 1, wherein the core has a minimum Distribution Index ($DI_{min}$) of about 2,950 g/m³ to about 3,200 g/m³.

11. The absorbent article of claim 1, wherein the core has a Distribution Index $_{i,j}$ ($DI_{i,j}$) at −5,0 of at least about 5,750 g/m³.

12. The absorbent article of claim 1, wherein the core has a Distribution Index $_{i,j}$ ($DI_{i,j}$) at 0,0 of at least about 6,000 g/m³.

13. The absorbent article of claim 1, wherein the core has a Distribution Index $_{i,j}$ ($DI_{i,j}$) at 5,0 of at least about 5,750 g/m³.

14. The absorbent article of claim 1, wherein the core has a Distribution Index $_{i,j}$ ($DI_{i,j}$) at 10,0 of at least about 4,250 g/m³.

15. The absorbent article of claim 1, wherein the core has a Distribution Index $_{i,j}$ ($DI_{i,j}$) at 15,0 of at least about 3,250 g/m³.

16. The absorbent article of claim 1, wherein the core has a Distribution Index $_{i,j}$ ($DI_{i,j}$) of at least 5,500 g/m³ at each point along a centerline of the core from −5,0 to 5,0.

17. The absorbent article of claim 1, wherein the $DI_{max}$ corresponds to a section of the core between 0,0 and 5,0.

18. An absorbent article comprising:
a core comprised of pulp, a polymer or a combination thereof;
wherein the core has a Distribution Index $_{i,j}$($DI_{i,j}$) at −5,0 of at least about 5,750 g/m3 or a Distribution Index i,j ($DI_{i,j}$) at 10,0 of at least about 4,250 g/m3, said ($DI_{i,j}$) being determined according to Formula I:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

by using the Baker Method.

19. The absorbent article of claim 18, wherein the core is comprised of about 10% to about 90% by weight of particulate or fibrous SAP.

20. The absorbent article of claim 18, wherein the core is comprised of about 20% to about 80% by weight of particulate or fibrous SAP.

21. The absorbent article of claim 18, wherein the polymer is SAP and is substantially homogeneous throughout the core.

22. The absorbent article of claim 18, wherein the core is comprised of about 40% to about 70% by weight of particulate or fibrous SAP.

23. An absorbent article comprising:
a core comprised of pulp, a polymer or a combination thereof;
wherein the core has a Distribution Index i,j ($DI_{i,j}$) at −5,0 of at least about 5,750 g/m3;
wherein the core has a Distribution Index i,j ($DI_{i,j}$) at 0,0 of at least about 6,000 g/m3;
wherein the core has a Distribution Index i,j ($DI_{i,j}$) at 5,0 of at least about 5750 g/m3;
wherein the core has a Distribution Index i,j ($DI_{i,j}$) at 10,0 of at least about 4,250 g/m3;
wherein the core has a Distribution Index (DI) at $_{i,j}$=15,0 of at least about 3,250 g/m3, and
wherein said ($DI_{i,j}$) is determined according to Formula I:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

by using the Baker Method.

24. An absorbent article comprising:
a core comprised of pulp, a polymer or a combination thereof; said core having a first Distribution Index ($DI_{male}$) measured at a male insult point and a second Distribution Index ($DI_{female}$) measured at a female insult point, said $DI_{male}$ being the DI(i,j) at the male insult point and said $DI_{female}$ being the DI(i,j) at the female insult point;
wherein the difference between the $DI_{male}$ and the $DI_{female}$ is at most about 1,000 g/m3, and
wherein said ($DI_{i,j}$) is determined according to Formula I:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

by using the Baker Method.

25. The absorbent article of claim 24, wherein the difference between the $DI_{male}$ and the $DI_{female}$ is at most about 900 g/m³.

26. The absorbent article of claim 24, wherein the difference between the $DI_{male}$ and the $DI_{female}$ is at most about 600 g/m³.

27. The absorbent article of claim 24, wherein the difference between the $DI_{male}$ and the $DI_{female}$ is at most about 400 g/m³.

28. The absorbent article of claim 24, wherein the $DI_{male}$ and the $DI_{female}$ are substantially the same.

29. The absorbent article of claim 24, wherein the $DI_{male}$ is at least about 4,200 g/m³.

30. The absorbent article of claim 24, wherein the $DI_{female}$ is at least about 5,500 g/m³.

31. The absorbent article of claim 24, wherein $DI_{max}$ of the article corresponds to a point on the centerline about equidistant between the male insult point and the female insult point.

32. The absorbent article of claim 24, wherein the core is comprised of about 10% to about 90% by weight of particulate or fibrous SAP.

33. The absorbent article of claim 24, wherein the core is comprised of about 20% to about 80% by weight of particulate or fibrous SAP.

34. The absorbent article of claim 24, wherein the polymer is SAP and is substantially homogeneous throughout the core.

35. The absorbent article of claim 24, wherein the core is comprised of about 40% to about 70% by weight of particulate or fibrous SAP.

36. An absorbent article comprising:
a core comprised of pulp, a polymer or a combination thereof; said core being said core being designed to provide a predetermined characteristic using general formula I:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

wherein N is the total number of core cells of the core, each core cell of the core corresponding to each of a plurality of 0.75 inch squares on a predetermined grid;
wherein T is each positive integer from 1 to N, each positive integer corresponding to each core cell of the core in numerical order;
wherein $DIST_T$ is a distance in centimeters (cm) between the center of the core cell corresponding to T and point i,j;
wherein $BW_T$ is the basis weight of each core cell, each core cell corresponding to each value for T;
wherein i,j is a coordinate representing a point on the core; and
wherein said $(DI_{i,j})$ is determined by using the Baker Method.

37. The absorbent article of claim 36, wherein the core has a DI of at least about 6,000 g/m³.

38. The absorbent article of claim 36, wherein the core has a DI of at least about 6,500 g/m³.

39. The absorbent article of claim 36, wherein the core has a DI of at least about 7,000 g/m³.

40. The absorbent article of claim 36, wherein the predetermined characteristic is optimal absorbency, optimal cost efficiency, optimal compatibility for males and females, optimal comfort, optimal appearance or combinations thereof.

41. An absorbent article prepared by a process comprising
forming a core according to a predetermined maximum Distribution Index ($DI_{max}$), said $DI_{max}$ being the maximum ($DI_{i,j}$) on the core, said ($DI_{i,j}$) being determined according to Formula I:

$$DI_{(i,j)}\left(\frac{g}{m^2}\right) = \frac{100\left(\frac{cm}{m}\right)}{N} \sum_{T=1}^{N} \frac{BW_T}{(Dist_T + 7.62)} \quad (I)$$

by using the Baker Method; and
placing or forming the core into an absorbent article;
wherein the core is comprised of pulp, a polymer or a combination thereof.

42. The absorbent article of claim 41, wherein the $DI_{max}$ is at least about 6,500 g/m³.

43. The absorbent article of claim 41, wherein the $DI_{max}$ is at least about 7,000 g/m³.

44. The absorbent article of claim 41, wherein the $DI_{max}$ is at least about 7,500 g/m³.

45. The absorbent article of claim 41, wherein the core is comprised of about 10% to about 90% by weight of particulate or fibrous SAP.

46. The absorbent article of claim 41, wherein the core is comprised of about 20% to about 80% by weight of particulate or fibrous SAP.

47. The absorbent article of claim 41, wherein the core is comprised of about 40% to about 70% by weight of particulate or fibrous SAP.

48. The absorbent article of claim 41, wherein the core has a minimum Distribution Index ($DI_{min}$) of about 2,800 g/m³ to about 3,600 g/m³.

49. The absorbent article of claim 41, wherein the core has a minimum Distribution Index ($DI_{min}$) of about 2,900 g/m³ to about 3,300 g/m³.

50. The absorbent article of claim 41, wherein the core has a minimum Distribution Index ($DI_{min}$) of about 2,950 g/m³ to about 3,200 g/m³.

51. The absorbent article of claim 41, wherein the core has a Distribution Index $_{i,j}$ ($DI_{i,j}$) at −5,0 of at least about 5,750 g/m³.

52. The absorbent article of claim 41, wherein the core has a Distribution Index $_{i,j}$ ($DI_{i,j}$) at 0,0 of at least about 6,000 g/m³.

53. The absorbent article of claim 41, wherein the core has a Distribution Index $_{i,j}$ ($DI_{i,j}$) at 5,0 of at least about 5,750 g/m³.

54. The absorbent article of claim 41, wherein the core has a Distribution Index $_{i,j}$ ($DI_{i,j}$) at 10,0 of at least about 4,250 g/m³.

55. The absorbent article of claim 41, wherein the core has a Distribution Index $_{i,j}$ ($DI_{i,j}$) at 15,0 of at least about 3,250 g/m³.

56. The absorbent article of claim 41, wherein the core has a Distribution Index of at least 5,500 g/m³ at each point along a centerline of the core from 0,0 to 5,0.

57. The absorbent article of claim 41, wherein the $DI_{max}$ corresponds to a a section on the core between 0,0 and 5,0.

58. An absorbent article prepared by a process comprising:
forming a core having a Distribution Index (DI) at i,j=0,0 of at least about 4750 g/m3 or a Distribution Index (DI) at i,j=12,0 of at least about 5750 g/m3, said DI i,j being determined by using the Baker Method; and
placing or forming the core into an absorbent article;
wherein the core is comprised of pulp, a polymer or a combination thereof.

59. An absorbent article prepared by a process comprising:
forming a core having a Distribution Index $_{i,j}$($DI_{i,j}$) at −5,0 of at least about 5,750 g/m³, a Distribution Index $_{i,j}$ ($DI_{i,j}$) at 0,0 of at least about 6,000 g/m³, a Distribution Index $_{i,j}$($DI_{i,j}$) at 5,0 of at least about 5,750 g/m³, a Distribution Index $_{i,j}$($DI_{i,j}$) at 10,0 of at least about 4,250 g/m³; and a Distribution Index $_{i,j}$($DI_{i,j}$) at 15,0 of at least about 3,250 g/m³, said $DI_{i,j}$ being determined by using the Baker Method;
wherein the core is comprised of pulp, a polymer or a combination thereof.

60. An absorbent article prepared by a process comprising:
forming a core comprised of pulp, a polymer or a combination thereof; the core having a first Distribution Index ($DI_{male}$) measured at a male insult point and a second Distribution Index ($DI_{female}$) measured at a female insult point, said $DI_{male}$ being the DJ(i,j) at the male insult point and said $DI_{female}$ being the DI(i,j) at the female insult point;

wherein the difference between the $DI_{male}$ and the $DI_{female}$ is at most about 1,000 g/m$^3$.

61. The absorbent article of claim 60, wherein the difference between the $DI_{male}$ and the $DI_{female}$ is at most about 900 g/m$^3$.

62. The absorbent article of claim 60, wherein the difference between the $DI_{male}$ and the $DI_{female}$ is at most about 600 g/m$^3$.

63. The absorbent article of claim 60, wherein the difference between the $DI_{male}$ and the $DI_{female}$ is at most about 400 g/m$^3$.

64. The absorbent article of claim 60, wherein the $DI_{male}$ and the $DI_{female}$ are substantially the same.

65. The absorbent article of claim 60, wherein the $DI_{male}$ is at least about 4,200 g/m$^3$.

66. The absorbent article of claim 60, wherein the $DI_{female}$ is at least about 5,500 g/m$^3$.

67. The absorbent article of claim 60, wherein the $DI_{max}$ corresponds to a point on the centerline about equidistant between the male insult point and the female insult point.

68. An absorbent article prepared by a process comprising:

selecting a Distribution Index (DI) or Distribution Index (DI) profile;

forming a core wherein the DI or DI profile is characterized by the general formula (I):

$$DI_{(i,j)}\left(\frac{g}{m^2}\right) = \frac{100\left(\frac{cm}{m}\right)}{N}\sum_{T=1}^{N}\frac{BW_T}{(Dist_T + 7.62)} \quad (I)$$

as determined by using the Baker method;
wherein N is the total number of core cells of the core, each core cell of the core corresponding to each of a plurality of 0.75 inch squares on a predetermined grid;
wherein T is each positive integer from 1 to N, each positive integer corresponding to each core cell of the core in numerical order;
wherein $DIST_T$ is a distance in centimeters (cm) between the center of the core cell corresponding to T and point i,j;
wherein $BW_T$ is the basis weight of each core cell, each core cell corresponding to each value for T; and
wherein i,j is a coordinate representing a point on the core.

69. An absorbent article comprising:
a core comprised of pulp, a polymer or a combination thereof;
wherein the core has a Distribution Index $_{i,j}(DI_{i,j})$ that is substantially the same at a first insult point and a second insult point, the first insult point being the insult point at commencement of use of the absorbent article and the second insult point being the insult point after use of the absorbent article, said $DI_{i,j}$ being determined by the Baker Method.

70. The absorbent article of claim 69, wherein the core has a Distribution Index Profile tailored in accordance with the expected shift in position of the insult point over time resulting from sagging of an absorbent article during use.

71. The absorbent article of claim 69, wherein the Distribution Index$_{i,j}$ ($DI_{i,j}$) is substantially the same at every point on the core along a line between the first insult point and the second insult point.

72. The absorbent article of claim 69, wherein the absorbent article is a nighttime diaper.

73. The absorbent article of claim 69, wherein the absorbent article is a travel diaper.

74. The absorbent article of claim 69, wherein the absorbent article is an extended-use diaper.

75. A method for preparing an absorbent article comprising:

selecting a Distribution Index at a point on a core or selecting a Distribution Index profile for a core by using the Baker Method forming the core according to the selected Distribution Index or Distribution Index profile; and placing or forming the core into the absorbent article;

wherein the core is comprised of pulp, a polymer or a combination thereof.

76. A method for determining the Distribution Index (DI) of an absorbent article comprising:

obtaining a core;

removing a plurality of samples from the core each sample corresponding to a core cell;

determining the basis weight of each core cell;

determining the distance from the center of each core cell (T) to an insult point; and calculating the DI Index for the insult point according to general formula (I):

$$DI_{(i,j)}\left(\frac{g}{m^2}\right) = \frac{100\left(\frac{cm}{m}\right)}{N}\sum_{T=1}^{N}\frac{BW_T}{(Dist_T + 7.62)} \quad (I)$$

by using the Baker method;
wherein N is the total number of core cells of the core, each core cell of the core corresponding to each of a plurality of 0.75 inch squares on a predetermined grid;
wherein T is each positive integer from 1 to N, each positive integer corresponding to each core cell of the core in numerical order;
wherein $DIST_T$ is a distance in centimeters (cm) between the center of the core cell corresponding to T and point i,j;
wherein $BW_T$ is the basis weight of each core cell, each said core cell corresponding to each value for T; and
wherein i,j is a coordinate representing a point on the core.

* * * * *